United States Patent
Song et al.

(10) Patent No.: US 8,404,812 B2
(45) Date of Patent: Mar. 26, 2013

(54) EPITOPE OF CD66C SPECIFIC TO LUNG ADENOCARCINOMA AND ANTIBODY RECOGNIZING THE SAME

(75) Inventors: Hyung-Geun Song, Cheongju-si (KR); Sang-Sun Yoon, Iksan-si (KR); Mi-Hyang Shin, Seongnam-si (KR); Yu-Ri Moon, Cheongju-si (KR)

(73) Assignee: Dinona Inc., Seoul (KR)

( * ) Notice: Subject to any disclaimer, the term of this patent is extended or adjusted under 35 U.S.C. 154(b) by 151 days.

(21) Appl. No.: 12/868,811

(22) Filed: Aug. 26, 2010

(65) Prior Publication Data

US 2011/0212095 A1    Sep. 1, 2011

(30) Foreign Application Priority Data

Feb. 26, 2010   (KR) .................. 10-2010-0018078
Jul. 29, 2010   (KR) .................. 10-2010-0073553

(51) Int. Cl.
    *C07K 16/00*    (2006.01)
    *C12N 5/07*     (2010.01)
    *G01N 33/53*    (2006.01)
    *A61K 39/395*   (2006.01)

(52) U.S. Cl. .................. 530/387.1; 530/388.1; 435/326; 435/7.1; 424/130.1

(58) Field of Classification Search ........................ None
    See application file for complete search history.

(56) References Cited

U.S. PATENT DOCUMENTS

| 5,225,541 A | 7/1993 | Hackett |
| 2003/0068636 A1* | 4/2003 | Veiby ................................ 435/6 |
| 2006/0088521 A1 | 4/2006 | Mahadevan |

FOREIGN PATENT DOCUMENTS

EP    0098162    1/1984

OTHER PUBLICATIONS

Cancer information from National Institute of Cancer, Apr. 29, 2010, pp. 1-2.*
Vogelstein et al., Nature Medicine, 2004, 10(8): 789-799.*
Tagawagi,Y. et al., Primary structure of nonspecific cross reacting antigen (NCA), a member of carcinoembryonic antigen (CEA) gene family, deduced from cDNA sequence, Biochem. Biphys. Res.Commun., 1998,150 (1), 89-96.

* cited by examiner

*Primary Examiner* — Hong Sang
(74) *Attorney, Agent, or Firm* — Lexyoume IP Meister, PLLC.

(57) ABSTRACT

The present invention relates to epitope of CD66c specific to lung adenocarcinoma and antibody recognizing the same. The present invention relates to identifying epitope of CD66c specific to lung adenocarcinoma, antibody recognizing the same, cell lines producing the same and the applications in diagnosis, prevention and treatment of lung adenocarcinoma by using the same. The above CD66c epitope is specific to lung adenocarcinoma cells, and therefore the antibody or its fragment recognizing the epitope can be used in compositions to diagnose, treat and prevent lung adenocarcinoma cells.

11 Claims, 15 Drawing Sheets

A. anti-CD66c mAb (AP11) coating - method #1

B. anti-Human Ig Fc coating - method #2

C. anti-Human Ig coating - method #3

FIG. 14

SEQUENCE LISTING

<160> NUMBER OF SEQ ID NOS: 13

<210> SEQ ID NO 1
<211> LENGTH: 344
<212> TYPE: PRT
<213> ORGANISM: Artificial Sequence
<220> FEATURE:
<223> OTHER INFORMATION: CD66c

<400> SEQUENCE: 1

```
Met Gly Pro Pro Ser Ala Pro Pro Cys Arg Leu His Val Pro Trp Lys
 1               5                  10                  15

Glu Val Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Ala His Asn Leu Pro Gln Asn Arg Ile Gly
    50                  55                  60

Tyr Ser Trp Tyr Lys Gly Glu Arg Val Asp Gly Asn Ser Leu Ile Val
65                  70                  75                  80

Gly Tyr Val Ile Gly Thr Gln Gln Ala Thr Pro Gly Pro Ala Tyr Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Val Gln Asn Thr Thr Tyr
                165                 170                 175

Leu Trp Trp Val Asn Gly Gln Ser Leu Pro Val Ser Pro Arg Leu Gln
            180                 185                 190

Leu Ser Asn Gly Asn Met Thr Leu Thr Leu Leu Ser Val Lys Arg Asn
        195                 200                 205

Asp Ala Gly Ser Tyr Glu Cys Glu Ile Gln Asn Pro Ala Ser Ala Asn
    210                 215                 220

Arg Ser Asp Pro Val Thr Leu Asn Val Leu Tyr Gly Pro Asp Val Pro
225                 230                 235                 240
```

Thr Ile Ser Pro Ser Lys Ala Asn Tyr Arg Pro Gly Glu Asn Leu Asn
            245                 250                 255

Leu Ser Cys His Ala Ala Ser Asn Pro Pro Ala Gln Tyr Ser Trp Phe
        260                 265                 270

Ile Asn Gly Thr Phe Gln Gln Ser Thr Gln Glu Leu Phe Ile Pro Asn
            275                 280                 285

Ile Thr Val Asn Asn Ser Gly Ser Tyr Met Cys Gln Ala His Asn Ser
        290                 295                 300

Ala Thr Gly Leu Asn Arg Thr Thr Val Thr Met Ile Thr Val Ser Gly
305                 310                 315                 320

Ser Ala Pro Val Leu Ser Ala Val Ala Thr Val Gly Ile Thr Ile Gly
                325                 330                 335

Val Leu Ala Arg Val Ala Leu Ile
            340

<210> SEQ ID NO 2
<211> LENGTH: 276
<212> TYPE: PRT
<213> ORGANISM: Artificial Sequence
<220> FEATURE:
<223> OTHER INFORMATION: Recombinant CD66c

<400> SEQUENCE: 2

Lys Leu Thr Ile Glu Ser Thr Pro Phe Asn Val Ala Glu Gly Lys Glu
1               5                   10                  15

Val Leu Leu Leu Ala His Asn Leu Pro Gln Asn Arg Ile Gly Tyr Ser
            20                  25                  30

Trp Tyr Lys Gly Glu Arg Val Asp Gly Asn Ser Leu Ile Val Gly Tyr
        35                  40                  45

Val Ile Gly Thr Gln Gln Ala Thr Pro Gly Pro Ala Tyr Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro Glu Leu Pro Lys
            100                 105                 110

Pro Ser Ile Ser Ser Asn Asn Ser Asn Pro Val Glu Asp Lys Asp Ala
        115                 120                 125

Val Ala Phe Thr Cys Glu Pro Glu Val Gln Asn Thr Thr Tyr Leu Trp
    130                 135                 140

Trp Val Asn Gly Gln Ser Leu Pro Val Ser Pro Arg Leu Gln Leu Ser
145                 150                 155                 160

Asn Gly Asn Met Thr Leu Thr Leu Leu Ser Val Lys Arg Asn Asp Ala
                165                 170                 175

Gly Ser Tyr Glu Cys Glu Ile Gln Asn Pro Ala Ser Ala Asn Arg Ser
            180                 185                 190

Asp Pro Val Thr Leu Asn Val Leu Tyr Gly Pro Asp Val Pro Thr Ile
        195                 200                 205

Ser Pro Ser Lys Ala Asn Tyr Arg Pro Gly Glu Asn Leu Asn Leu Ser
    210                 215                 220

Cys His Ala Ala Ser Asn Pro Pro Ala Gln Tyr Ser Trp Phe Ile Asn
225                 230                 235                 240

Gly Thr Phe Gln Gln Ser Thr Gln Glu Leu Phe Ile Pro Asn Ile Thr
                245                 250                 255

```
Val Asn Asn Ser Gly Ser Tyr Met Cys Gln Ala His Asn Ser Ala Thr
            260                 265                 270

Gly Leu Asn Arg
        275

<210> SEQ ID NO 3
<211> LENGTH: 27
<212> TYPE: DNA
<213> ORGANISM: Artificial Sequence
<220> FEATURE:
<223> OTHER INFORMATION: CD66c gene forward primer

<400> SEQUENCE: 3
aagcttaagc tcactattga atccacg                                            27

<210> SEQ ID NO 4
<211> LENGTH: 26
<212> TYPE: DNA
<213> ORGANISM: Artificial Sequence
<220> FEATURE:
<223> OTHER INFORMATION: CD66c gene reverse primer

<400> SEQUENCE: 4
gatatcagtg actgtggtcc tattga                                             26

<210> SEQ ID NO 5
<211> LENGTH: 27
<212> TYPE: DNA
<213> ORGANISM: Artificial Sequence
<220> FEATURE:
<223> OTHER INFORMATION: HuIgFc forward primer

<400> SEQUENCE: 5
gatatcgacg tcgagtccaa atcttgt                                            27

<210> SEQ ID NO 6
<211> LENGTH: 26
<212> TYPE: DNA
<213> ORGANISM: Artificial Sequence
<220> FEATURE:
<223> OTHER INFORMATION: HuIgFc reverse primer

<400> SEQUENCE: 6
ctcgagttta cccggagaca gggaga                                             26

<210> SEQ ID NO 7
<211> LENGTH: 19
<212> TYPE: PRT
<213> ORGANISM: Artificial Sequence
<220> FEATURE:
<223> OTHER INFORMATION: epitope of 8F5 monoclonal antibody

<400> SEQUENCE: 7

Arg Asn Asp Ala Gly Ser Tyr Glu Cys Glu Ile Gln Asn Pro Ala Ser
  1               5                  10                  15

Ala Asn Arg

<210> SEQ ID NO 8
<211> LENGTH: 831
<212> TYPE: DNA
<213> ORGANISM: Artificial Sequence
<220> FEATURE:
<223> OTHER INFORMATION: CD66c cDNA-hydrophobic region

<400> SEQUENCE: 8
actattgaat ccacgccgtt caatgtcgca gaggggaagg aggttctcct actcgcccac        60
```

-continued

```
aacctgcccc agaatcgtat tggttacagc tggtacaaag gcgaaagagt ggatggcaac      120
agtctaattg taggatatgt aataggaact caacaagcta ccccagggcc cgcatacagt      180
ggtcgagaga caatataccc caatgcatcc ctgctgatcc agaacgtcac ccagaatgac      240
acaggattct ataccctaca agtcataaag tcagatcttg tgaatgaaga agcaaccgga      300
cagttccatg tatacccgga gctgcccaag ccctccatct ccagcaacaa ctccaacccc      360
gtggaggaca aggatgctgt ggccttcacc tgtgaacctg aggttcagaa cacaacctac      420
ctgtggtggg taaatggtca gagcctcccg gtcagtccca ggctgcagct gtccaatggc      480
aacatgaccc tcactctact cagcgtcaaa aggaacgatg caggatccta tgaatgtgaa      540
atacagaacc cagcgagtgc caaccgcagt gacccagtca ccctgaatgt cctctatggc      600
ccagatggcc ccaccatttc cccctcaaag gccaattacc gtccagggga aaatctgaac      660
ctctcctgcc acgcagcctc taacccacct gcacagtact cttggtttat caatgggacg      720
ttccagcaat ccacacaaga gctctttatc cccaacatca ctgtgaataa tagcggatcc      780
tatatgtgcc aagcccataa ctcagccact ggcctcaata ggaccacagt c              831

<210> SEQ ID NO 9
<211> LENGTH: 600
<212> TYPE: DNA
<213> ORGANISM: Artificial Sequence
<220> FEATURE:
<223> OTHER INFORMATION: CD66c mutant(BI /BHI)

<400> SEQUENCE: 9
aagcttaagc tcactattga atccacgccg ttcaatgtcg cagaggggaa ggaggttctt       60
ctactcgccc acaacctgcc ccagaatcgt attggttaca gctggtacaa aggcgaaaga      120
gtggatggca acagtctaat tgtaggatat gtaataggaa ctcaacaagc taccccaggg      180
cccgcataca gtggtcgaga gacaatatac cccaatgcat ccctgctgat ccagaacgtc      240
acccagaatg acacaggatt ctataccta caagtcataa agtcagatct tgtgaatgaa      300
gaagcaaccg acagttcca tgtatacccg gagctgccca gccctccat ctccagcaac      360 aactccaacc ccgtggagga caaggatgct gtggccttca cctgtgaacc tgaggttcag      420
aacacaacct acctgtggtg ggtaaatggt cagagcctcc cggtcagtcc caggctgcag      480
ctgtccaatg gcaacatgac cctcactcta ctcagcgtca aaaggaacga tgcaggatcc      540
tatatgtgcc aagcccataa ctcagccact ggcctcaata ggaccacagt cacggatatc      600

<210> SEQ ID NO 10
<211> LENGTH: 378
<212> TYPE: DNA
<213> ORGANISM: Artificial Sequence
<220> FEATURE:
<223> OTHER INFORMATION: CD66c mutant(HPK/HdIII/PstI/klenow)

<400> SEQUENCE: 10
aagctgctgt ccaatggcaa catgaccctc actctactca gcgtcaaaag gaacgatgca       60
ggatcctatg aatgtgaaat acagaaccca gcgagtgcca accgcagtga cccagtcacc      120
ctgaatgtcc tctatggccc agatgtcccc accatttccc cctcaaaggc caattaccgt      180
ccaggggaaa atctgaacct ctcctgccac gcagcctcaa acccacctgc acagtactct      240
tggtttatca atgggacgtt ccagcaatcc acacaagagc tctttatccc caacatcact      300
gtgaataata gcggatccta tatgtgccaa gcccataact cagccactgg cctcaatagg      360
accacagtca cggatatc                                                    378
```

```
<210> SEQ ID NO 11
<211> LENGTH: 705
<212> TYPE: DNA
<213> ORGANISM: Artificial Sequence
<220> FEATURE:
<223> OTHER INFORMATION: Human immunoglobulin Fc region CH2-CH3

<400> SEQUENCE: 11
gacgtcgagt ccaaatcttg tgacaaaact cacacatgcc caccgtgccc agcacctgaa        60
ctcctggggg gaccgtcagt cttcctcttc cccccaaaac ccaaggacac cctcatgatc       120
tcccggaccc ctgaggtcac atgcgtggtg gtggacgtga gccacgaaga ccctgaggtc       180
aagttcagct ggtacgtgga cggcgtggag gtgcataatg ccaagacaaa gccgcgggag       240
gagcagtaca acagcacgta ccgtgtggtc agcgtcctca ccgtcctgca ccaggactgg       300
ctgaatggca aggagtacaa gtgcaaggtc tccaacaaag ccctcccagc ccccatcgag       360
aaaaccatct ccaaagccaa agggcagccc cgagaaccac aggtgtacac cctgccccca       420
tcccgagagg agatgaccaa gaaccaggtc agcctgacct gcctggtcaa aggcttctat       480
cccagcgaca tcgccgtgga gtgggagagc aatgggcagc cggagaacaa ctacaagacc       540
acgcctcccg tgctggactc cgacggctcc ttcttcctct atagcaagct caccgtggac       600
aagagcaggt ggcagcaggg gaacgtcttc tcatgctccg tgatgcatga ggctctgcac       660
aaccactaca cgcagaagag cctctccctg tctccgggta aatga                       705

<210> SEQ ID NO 12
<211> LENGTH: 288
<212> TYPE: PRT
<213> ORGANISM: Artificial Sequence
<220> FEATURE:
<223> OTHER INFORMATION: CD66c recombinants

<400> SEQUENCE: 12

Lys Leu Lys Leu Thr Ile Glu Ser Thr Pro Phe Asn Val Ala Glu Gly
  1               5                  10                  15

Lys Glu Val Leu Leu Ala His Asn Leu Pro Gln Asn Arg Ile Gly
             20                  25                  30

Tyr Ser Trp Tyr Lys Gly Glu Arg Val Asp Gly Asn Ser Leu Ile Val
         35                  40                  45

Gly Tyr Val Ile Gly Thr Gln Gln Ala Thr Pro Gly Pro Ala Tyr Ser
     50                  55                  60

Gly Arg Glu Thr Ile Tyr Pro Asn Ala Ser Leu Leu Ile Gln Asn Val
 65                  70                  75                  80

Thr Gln Asn Asp Thr Gly Phe Tyr Thr Leu Gln Val Ile Lys Ser Asp
                 85                  90                  95

Leu Val Asn Glu Glu Ala Thr Gly Gln Phe His Val Tyr Pro Glu Leu
            100                 105                 110

Pro Lys Pro Ser Ile Ser Ser Asn Asn Ser Asn Pro Val Glu Asp Lys
        115                 120                 125

Asp Ala Val Ala Phe Thr Cys Glu Pro Glu Val Gln Asn Thr Thr Tyr
    130                 135                 140

Leu Trp Trp Val Asn Gly Gln Ser Leu Pro Val Ser Pro Arg Leu Gln
145                 150                 155                 160

Leu Ser Asn Gly Asn Met Glu Thr Thr Leu Thr Leu Ser Val Lys
                165                 170                 175

Arg Asn Asp Ala Gly Ser Tyr Glu Cys Glu Ile Gln Asn Pro Ala Ser
            180                 185                 190
```

```
Ala Asn Arg Ser Asp Pro Val Thr Leu Asn Val Leu Tyr Gly Pro Asp
            195                 200                 205

Val Pro Thr Ile Ser Pro Ser Lys Ala Asn Tyr Arg Pro Gly Glu Asn
    210                 215                 220

Leu Asn Leu Ser Cys His Ala Ala Ser Asn Pro Pro Ala Gln Tyr Ser
225                 230                 235                 240

Trp Phe Ile Asn Gly Thr Phe Gln Gln Ser Thr Gln Glu Leu Phe Ile
            245                 250                 255

Pro Asn Ile Thr Val Asn Asn Ser Gly Ser Tyr Met Glu Thr Cys Gln
            260                 265                 270

Ala His Asn Ser Ala Thr Gly Leu Asn Arg Thr Thr Val Thr Asp Ile
            275                 280                 285

<210> SEQ ID NO 13
<211> LENGTH: 27
<212> TYPE: PRT
<213> ORGANISM: Artificial Sequence
<220> FEATURE:
<223> OTHER INFORMATION: peptide (Query 120) shown in Fig. 14

<400> SEQUENCE: 13

Leu Thr Ile Glu Ser Thr Pro Phe Asn Val Ala Glu Gly Lys Glu Val
  1               5                  10                  15

Leu Leu Leu Ala His Asn Leu Pro Gln Asn Arg
             20                  25
```

EPITOPE OF CD66C SPECIFIC TO LUNG ADENOCARCINOMA AND ANTIBODY RECOGNIZING THE SAME

CROSS REFERENCE TO RELATED APPLICATION

The present application claims the priority of Application Serial No. 10-2010-0018078, filed on Feb. 26, 2010, and Application Serial No. 10-2010-0073553, filed on Jul. 29, 2010, and contains all the contents of said applications as a reference.

FIELD OF THE INVENTION

The present invention relates to epitope of CD66c specific to lung adenocarcinoma and antibody recognizing the same. The present invention relates to identifying epitope of CD66c specific to lung adenocarcinoma, antibody recognizing the same, cell lines producing the same and the applications in diagnosis, prevention and treatment of lung adenocarcinoma by using the same.

BACKGROUND OF THE INVENTION

Lung cancer is one of the frequently occurring cancers in the world that threatens the lives of the human population. About 1.2 million people contract lung cancer world-wide and about 25% of the cancer-related deaths are due to lung cancer. Also, the occurrence rate and the death rate are gradually increasing in Korea. According to a report of Korea Central Cancer Registry in 2008, there were 132,941 cancer incidences in average in Korea in the periods of 2003-2005, and 16,123 lung cancer incidences in annual average for male and female indicating that 12.1% of total cancers are lung cancer placing second most commonly occurring cancer in Korea (Ministry of Health & Welfare, Korea Central Cancer Registry, Oct. 15, 2008).

It is known that a 5-year survival rate of lung cancer exceeds 80% if the lung cancer was found early in IA stage (Mulshine, J. L. and Sullivan, D. C. Clinical practice. Lung cancer screening. *N. Engl. J. Med.* 2005; 352:2714-2720). It is therefore important to find good markers that enables early discovery of lung cancer in pursuit of specific biological markers. Especially, lung cancer is a representative heterogeneous tumor, and the response and the prognosis are different for a variety of treatments. Lung cancer can be divided into two major categories medically, small cell lung cancer and non-small cell lung cancers (NSCLC). Non-small cell lung cancers can be further divided into lung adenocarcinoma, squamous cell carcinoma and large cell carcinoma.

Meanwhile, CD66c is known as CEACAM6 (Carcinoembryonic antigen-related cell adhesion molecule 6) or NCA (non-specific cross-reacting glycoprotein antigen)-90 and has a higher concentration in the blood of lung cancer, pancreatic cancer, breast cancer, rectal cancer and hepatoma patients. The above CD66c is an important protein for cell adhesion and is involved in adhesion of endothelial cells activated by cytokine in case of neutrophils.

Also, normal cells destroy themselves if cell adhesion is prevented. This process is called anoikis. Tumor cells, however, are resistant to such anoikis and promote cancer outbreak and metastasis of cancer as a result. There is a report that the above CD66c prevents anoikis, and there also is a report that malignant phenotype changes in cancer cells by regulating the expression of CD66c. Also, when the protein expression is inhibited by silencing CD66c genes by using small interfering RNA, metastasis is inhibited by enhancement of anoikis in vivo. In conclusion, metastasis can be prevented by inhibiting the function of CD66c.

SUMMARY OF THE INVENTION

In order to develop antibody specific to CD66c that is expressed in lung adenocarcinoma cells, the present inventors have completed the present invention by developing an antibody for CD66c specific to lung adenocarcinoma by immunizing lung adenocarcinoma cell line with CD66c recombinant antigen.

Therefore the object of the present invention is to provide an isolated polypeptide comprising an epitope of CD66c (Cluster of Differentiation 66c) represented by amino acid sequence of SEQ ID: 7.

Also the object of the present invention is to provide an antibody or its fragment recognizing the isolated polypeptide as an epitope.

Also the object of the invention is to provide a cell line producing the antibody or its fragment.

Also the object of the present invention is to provide a composition for diagnosing lung adenocarcinoma comprising the antibody or its fragment specific to lung adenocarcinoma as an effective ingredient.

Also the object of the present invention is to provide a diagnostic kit for lung adenocarcinoma comprising the antibody or its fragment specific to lung adenocarcinoma as an effective ingredient.

Also the object of the present invention is to provide a pharmaceutical composition for preventing or treating lung adenocarcinoma comprising the antibody or its fragment specific to lung adenocarcinoma of claim 3 as an effective ingredient.

Also the object of the present invention is to provide a method of diagnosing lung adenocarcinoma comprising incubating cells in a biological sample with the antibody or its fragment, and detecting the positive immune reaction to the antibody or its fragment.

Also the object of the present invention is to provide a method of treating lung adenocarcinoma comprising administering a therapeutically effective amount of the antibody or its fragment to a patient in need of treating lung adenocarcinoma.

BRIEF DESCRIPTION OF THE DRAWINGS

FIGS. 4A-4C each denotes a result of the expression of CD66c-HuIgFc recombinant antigen by performing ELISA using AP11, an antibody of CD66c (FIG. 4A), Goat anti-human Fc fragment (FIG. 4B), and Goat anti-human Ig (FIG. 4C).

FIG. 6A is a result showing a negative response for A549 lung adenocarcinoma cell lines stained with FITC-labeled goat anti-mouse IgM.

FIG. 6B is a result showing a positive response for pre-incubated AP11 mAb and a FITC-labeled goat anti-mouse IgM stained with A549 cells.

FIGS. 6C-6E are results showing the blockage of Ap11 and A549 cells reaction when CD66c-HuIgFc was conjugated with 10 μg (FIG. 6C), 50 μg (FIG. 6D), and 100 μg (FIG. 6E) of anti-CD66c mAb and conjugated subsequently with A549 cells.

FIGS. 13A and 13B are results confirming a brown positive response in the lung adenocarcinoma tissues.

FIGS. 13C-13D are results showing a negative response for squamous cell carcinoma tissue (FIG. 13C) and small cell carcinoma tissues (FIG. 13D).

FIG. 14 is a result of confirming the epitope of monoclonal antibody of the present invention by performing MOLDI-TOF.

DETAILED DESCRIPTION OF THE EMBODIMENTS

Figure 1:
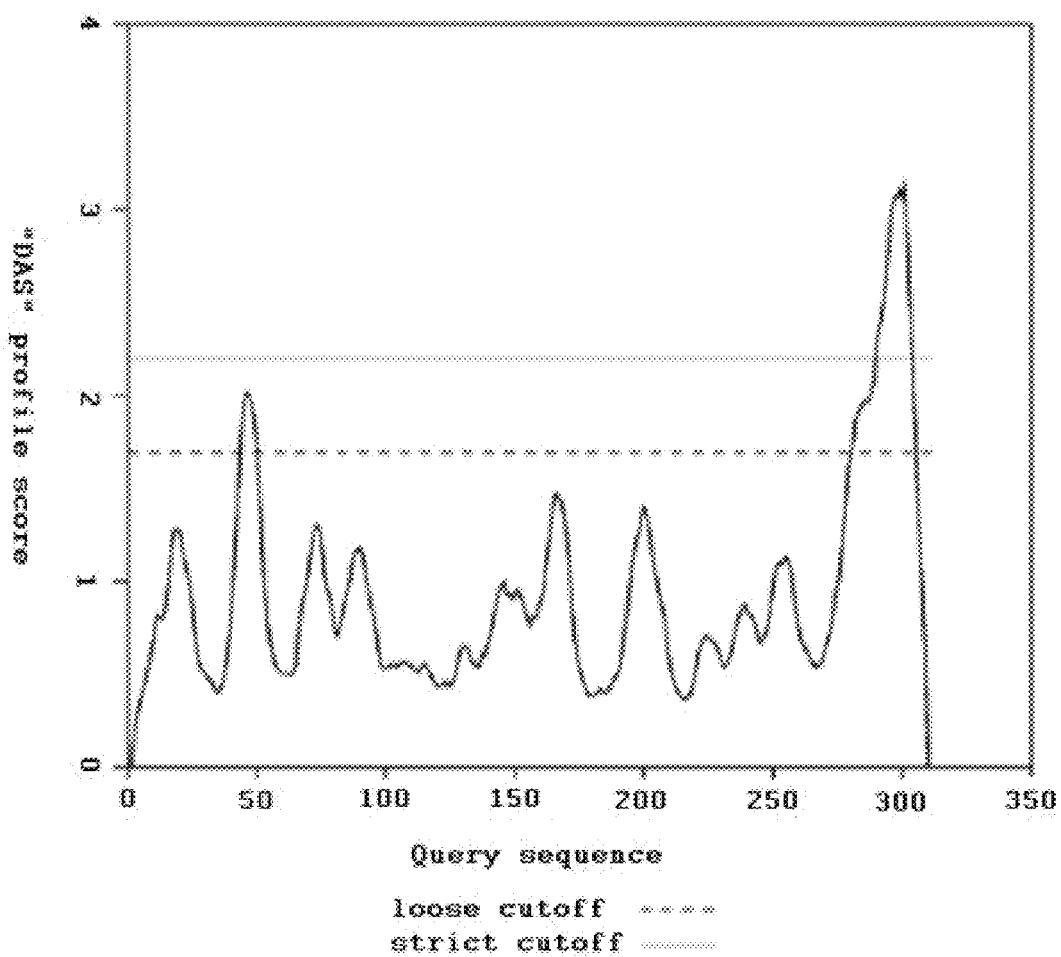
FIG. 1 is a drawing representing the result of setting up the recombinant region of CD66c.

In order to solve the above problems, the present inventors provides an isolated polypeptide comprising an epitope of CD66c (Cluster of Differentiation 66c) represented by amino acid sequence of SEQ ID: 7.

Also the present invention provides an antibody or its fragment recognizing the isolated polypeptide as an epitope.

Also the present invention provides a cell line producing the antibody or its fragment.

Also the present invention provides a composition for diagnosing lung adenocarcinoma comprising the antibody or its fragment specific to lung adenocarcinoma as an effective ingredient.

Also the present invention provides a diagnostic kit for lung adenocarcinoma comprising the antibody or its fragment specific to lung adenocarcinoma as an effective ingredient.

Also the present invention provides a pharmaceutical composition for preventing or treating lung adenocarcinoma comprising the antibody or its fragment specific to lung adenocarcinoma of claim 3 as an effective ingredient.

Also the present invention provides a method of diagnosing lung adenocarcinoma comprising incubating cells in a biological sample with the antibody or its fragment, and detecting the positive immune reaction to the antibody or its fragment.

Also the present invention provides a method of treating lung adenocarcinoma comprising administering a therapeutically effective amount of the antibody or its fragment to a patient in need of treating lung adenocarcinoma.

In below the present invention is explained in detail.

Cluster of Differentiation 66c (CD66c) is a protein known as carcinoembryonic antigen-related cell adhesion molecule 6 (CEACAM 6) or non-specific cross-reacting glycoprotein antigen (NCA)-90 and as an important protein for cell adhesion. CD66c can be represented preferably, but not limited to, amino acid sequence of SEQ ID No: 1 (Genebank Protein No. AAH05008).

An epitope in the present invention is a conformational determinants of an antigen is preferably, but not limited to, a linear epitope.

An antibody in the present invention is a polypeptide or its fragment containing the framework region from the immunoglobulin gene, and an antibody specifically binds to and recognizes its antigen. Recognized immunoglobulin gene includes a recognized immunoglobulin gene includes kappa, lambda, alpha, gamma, delta, epsilon and mu conserved region in gene sequence and a variety of variable region in gene sequence. A light chain can be divided into kappa and lambda. A heavy chain can be divided into gamma, mu, alpha, delta or epsilon, and defined as immunoglobulin class IgG, IgM, IgA, IgD and IgE, respectively. Especially the antibody in the present invention includes chimeric and humanized antibodies.

The chimeric antibody in the present invention is an antibody that the sequence in the variable region is from one species and the sequence in the conserved region is from other species; for example, the variable region is from mouse and the sequence in the conserved region is from human.

The humanized antibody in the present invention is an antibody with low immunogenicity and with activity of non-human antibody. It can be prepared by keeping non-human CDR region and substitute the rest of the region with human counterparts. For example, the below literature is referenced: Morrison et al, Proc. Natl. Acad. Sci. USA, 81:6851-6855 (1984); Morrison and Oi, Adv. Immunol., 44:65-92 (1988); Verhoeyen et al, Science, 239:1534-1536 (1988); Padlan, Molec. Immun., 28:489-498 (1991); Padlan, Molec. Immun., 31(3):169-217 (1994).

The antibody fragment in the present invention is not limited if it recognizes specifically CD66c epitope including variable region of a light chain ($V_L$) and variable region of a heavy chain ($V_H$), but can be selected from a group containing Fab, Fab', F(ab')2, scFv, dsFv and CDR. Especially, the scFv is an antibody fragment prepared as a single chain by connecting the variable region of a heavy chain ($V_H$) and variable region of a light chain ($V_L$) with a linker polypeptide The monoclonal antibody in the present invention is a terminology ordinary in the art, and is a highly specific antibody to a single antigen region. Conventionally unlike polyclonal antibody that includes different antibodies directed to different epitope, a monoclonal antibody is directed to a single epitope. The monoclonal antibody of the present invention can be prepared by conventional cloning or cell fusion technologies. For instance, natural or human monoclonal antibody can be produced by administrating antigen of the interest into a wild type or transgenic mice (BALB/c for example). Such antigen be administered alone or after mixing it with adjuvant, or expressed from a vector and immune response can be induced by DNA or fusion proteins. A fusion protein include intended peptide and coupled carrier peptide with immune response, for instance β-galactoxidase, glutathione-S-transferase, keyhole limpet hemocyanin (KLH) and bovine serum albumin, and carrier proteins are not limited to them. In the above case, the peptide acts as hapten to the carrier protein.

Preparation method of the above monoclonal antibody can be explained as follows. After boosting an animal, spleen is removed to extract spleen cells and fused with myeloma cells by using publicly known technology in the art [Kohler and Milstein, Nature 256: 495-497 (1975); and Harlow and Lane, Antibodies: A Laboratory Manual, Cold Spring Harbor Laboratory, New York (1988)]]. Acquired hybridoma cells are cloned by limiting dilution, and acquired dons producing monoclonal antibody are cultured.

The monoclonal antibody has an advantage to improve the selectivity and specificity in diagnosis and analysis using antigen-antibody interactions and not to contaminate by other immunoglobulin since it is synthesized by hybridoma cultivation.

The hybridoma cell in the present invention is well known in the art, and is a cell formed by antibody producing cells and immortalized cells, for instance myeloma cells. The above hybridoma cell can produce antibodies continuously.

The polyclonal antibody in the present invention can be produced by injecting antigens including the epitope of the present invention, and preferably a portion of CD66c of SEQ ID No: 2 into an animal and draw blood to collect serum containing the antibody. Such polyclonal antibody can be purified by any of the methods known in the art, and can be prepared from a host of a goat, a rabbit, a sheep, a monkey, a horse, a pig, a cow and a dog.

A detection probe in the present invention is a probe to detect the product of antigen-antibody interactions, more specifically includes, but not limited to, radioisotope probe, enzyme, chemoluminescent compound, fluorescent materials such as fluorescein, phycobiliprotein, rare earth chelate and rhodamine, enzyme cofactor and biotin.

The isolated polypeptide discovered to be an epitope of CD66c has a characteristic to be represented as amino acid sequence of SEQ ID No: 7.

The above epitope of CD66c is not limited to but preferably specific to lung adenocarcinoma.

In the embodiment of the present invention, the monoclonal antibody for CD66c specific to lung adenocarcinoma is developed (refer to Example 2) by immunizing lung adenocarcinoma cell line with CD66c recombinant antigens (refer to Example 1), and it is found for the first time that its epitope is amino acid sequence of SEQ ID No: 7 (refer to Example 3). Especially, the epitope of CD66c of the present invention is an epitope recognized specifically by monoclonal antibody (8F5) of the present invention unlike the conventional antibodies for CD66c, 9A6 (Santa Cruz biotechnology) or AP11 (DiNona) (refer to Example 3).

Therefore, the epitope of CD66c represented by amino acid sequence of SEQ ID: 7 of the present invention can be used as an effective ingredient of an immunogenic composition to induce the formation of the antibody specific to lung adenocarcinoma.

Therefore, another aspect of the present invention provides an immunogenic composition containing the isolated polypeptide comprising an epitope of CD66c (Cluster of Differentiation 66c) represented by amino acid sequence of SEQ ID: 7. The immunogenic composition could optionally contain pharmaceutically acceptable vehicles, including release-controlling agent. Said vehicles might further include pharmaceutically acceptable vectors or diluents suitable for the administration for treating lung adenocarcinoma. Suitable pharmaceutically acceptable vectors refer to those biologically inert and/or non-toxic. Various vectors known in the art can be selected according to desired use. Typically, said vector can be selected from but not limit to the group consisting of: sterile saline, lactose, sucrose, calcium orthophosphate, gelatin, dextrin, agar, alum, aluminum oxide, aluminum hydroxide, peanut oil, olive oil, sesame oil, and water. Additionally, vector or diluents can further include controlled released substance, such as glyceryl monostearate/glyceryl distearate, either alone or in combination with paraffin. In addition, conventional controlled release polymer formulation, including soluble glass can also be used.

The above epitope for CD66c can be separated from biological specimens, synthesized chemically, or produced by genetic engineering, and the above methods can be carried out easily by prior technologies.

Meanwhile, the antibody or its fragment of the present invention has a characteristic of recognizing the epitope of the present invention.

The antibody of the present invention is not limited to, but preferably to be monoclonal antibody or polyclonal antibody, and the above monoclonal antibody is preferably produced by hybridoma cell (deposition number: KCLRF-BP-00230).

Especially, the antibody of the present invention is, not limited to, but preferably IgG1 and categorized to include kappa light chain (refer to Example 2-2).

The antibody of the present invention is not limited to, but preferably an antibody specific to lung adenocarcinoma.

In the embodiment of the present invention, the antibody of the present invention is developed by immunizing lung adenocarcinoma cell line with recombinant antigen of a region of CD66c represented by SEQ ID No: 2 and Fc of human immunoglobulin G, and by screening antibody specific to the above antigen in order to prepare antibody specific to lung adenocarcinoma (refer to Example 2-2).

Meanwhile the cell line in the present invention has a characteristic of producing the above antibody or its fragments.

The above cell line is not limited to, but preferably to be hybridoma cells of deposition number KCLRF-BP-00230. The above hybridoma cell is a cell producing the above monoclonal antibody with its preparation method is well known in the field, and preferably can be produced by fusion between antibody producing cells and immortalized cells, for instance, myeloma cells. It can be prepared by cell fusion between preferably, but not limited to, myeloma cells (preferably X63-Ag8.653 cells) and mouse spleen cells immunized with lung adenocarcinoma cell line.

The above hybridoma cells are deposited as '8F5' to Korean Cell Line Research Foundation (KCLRF) on Feb. 22, 2010 with a deposition number KCLRF-BP-00230.

Meanwhile the diagnostic composition in the present invention has a characteristic of comprising the above antibody or its fragments.

The above antibody or antibody fragment specific to lung adenocarcinoma recognizes specifically the epitope of Cluster of Differentiation 66c (CD66c) represented by amino acid sequence of SEQ ID No: 7, detects CD66c antigen efficiently, and especially detect lung adenocarcinoma expressing CD66c antigen (refer to Example 4).

In case the above antibody or its fragment specific to lung adenocarcinoma is used in the above diagnostic composition, the above antibody or antibody fragment can be probed by the probes selected from a group of enzymes, radioisotopes, fluorescent materials, chromogens and dyes. The above fluorescent materials include, but not limited to, fluorescein isothiocyanate (FITC), phycoerythrin (PE), PE-Cy5, and allophycocyanin (APC).

The above diagnostic composition can include carrier for immunological analysis, detection probe for the production of detectable signal, solubilizer and cleaner besides the above or antibody fragment specific to lung adenocarcinoma. Also, it can include substrate and reaction stopper when the probe material is an enzyme. The above carriers are, not limited to, soluble carriers such as physiologically allowed buffer solutions (PBS for instance) known in the art, polymers such as magnetic microparticles made by insoluble carriers, such as polystyrene, polyethylene, polypropylene, polyester, polyacrylonitril, fluoride resin, cross-linked dextran, polysaccharide and latex, and coated with metal, paper, glass, metal agarose and the combinations of the same.

Meanwhile, the diagnostic kit of the present invention can diagnose lung adenocarcinoma effectively since it includes antibody or its fragment specific to the above adenocarcinoma.

The kit system for use in the present invention is not limited to, but include ELISA plate, dip-stick device, immunochromatography and radial partition immunoassay device and flow-through device. Preferably strip type or device type diagnostic kit using immunochromatography can be used. A diagnosis by immunochromatography can be distinguished to be positive or negative by naked eyes by reacting antigens in the serum of the specimen with tracer antibody bonded to colloidal gold particles and by forming a color strip by combining with capture antibody anchored on the internal surface of micropores while moving through the micropores of the nitrocellulose membrane by capillary actions.

The above kit can use, not limited to, but preferably enzyme-linked immunosorbent assay (ELISA) or lateral flow immunographic assay. As described above, when sandwich immunoassay or lateral flow immunographic assay is used, adenocarcinoma can be effectively diagnosed by preparing antibody pair using the adenocarcinoma specific antibody or antibody fragment of the present invention.

The above kit of the present invention is not limited if it is used in the conventional kit, but can include solid support, antibody or antibody fragment specific to adenocarcinoma of the present invention, enzyme-labeled antibody solution for the reaction with antigen and reaction solutions for Enzyme-linked immunosorbent assay (ELIZA) containing color developer for enzymatic reaction for ELISA. More specifically, enzyme-labeled antibody solution can be goat anti-mouse Ig-HRP, and color developer can be Tetramethylbenzidine (TMB) and reaction stopper can be HCl or $H_2SO_4$.

Meanwhile, the pharmaceutical composition for the prevention or treatment of lung adenocarcinoma of the present invention contains the above antibody or antibody fragment specific to lung adenocarcinoma as an active ingredient.

The antibody or its fragment specific to lung adenocarcinoma of the present invention has a superior inhibitory activity against cancer, especially lung adenocarcinoma (refer to Example 5).

Therefore, the pharmaceutical composition of the present invention can be used for the prevention or treatment of lung adenocarcinoma effectively by containing the above antibody or its fragment specific to lung adenocarcinoma.

The content of the above antibody or its fragment as an active ingredient in the pharmaceutical composition of the present invention can be adjusted depending on the usage type, objective, patient condition, symptomatic type and heaviness of disease, and preferably 0.1~50 weight %, more preferably 1~20 weight %, but not limited to the range.

The pharmaceutical composition of the present invention can be administered to mammals including human via a variety of routes. Any conventionally methods of administration can be used, for instance, oral, rectal, intravenous, intramuscular, subcutaneous, intraepidural or intracerebroventricular administrations can be used.

The pharmaceutical composition of the present invention can be formulated by conventional methods into oral formulations such as powders, granules, tablets, capsules, suspensions, emulsions, syrup, aerosol or non-oral formulations such as transcutaneous formulation, Rectal Suppository and sterilized solution for injection.

The pharmaceutical composition of the present invention can contain adjuvant such as pharmaceutically acceptable and physiologically allowed carriers, excipients and diluents besides the above extracts. The carrier, excipients and diluents included in the pharmaceutical composition of the present invention can be lactose, dextrose, sucrose, sorbitol, mannitol, xylitol, erythritol, maltitol, starch, acacia gum, alginate, gelatin, calcium phosphate, calcium silicate, cellulose, methyl cellulose, amorphous cellulose, polyvinyl pyrrolidone, water, methylhydroxybenzoate, propylhydroxybenzoate, talc, magnesium stearate and mineral oil. In case of formulation, commonly used diluents or excipients such as fillers, extender, binder, humectant, disintegrant and surfactant can be used. Solid formulations for oral administration include tablets, pills, powder, granules and capsules, and can be prepared by mixing the above extract of Radix Polygalae Tenuifoliae, Rhizoma et Radix Ligustici and Arillus Euphoriae Longanae with one or more excipients such as starch, calcium carbonate, sucrose, lactose or gelatin. Also lubricants such as magnesium stearate and talc can be used instead of a simple excipients.

Liquid formulations for oral administrations include suspension, liquid and solution, emulsion, syrup, and frequently used water, liquid paraffin and other excipients such as humectant, sweetener, aromatics and preservatives can also be used. In the formulations for non-oral administration, sterilized aqueous solution, non-aqueous solvent, suspension, emulsion, freeze-dried formulation, rectal suppository and transcutaneous formulation are included. Propylene glycol, polyethylene glycol, vegetable oil, such as olive oil, and injectable esters, such as ethyloleate, can be used as non-aqueous solvent or suspension. The base for suppository includes witepsol, macrogol, tween 61, cacao oil, laurin oil, glycerol and gelatin.

The pharmaceutical composition of the present invention can be administered to human as a single formulation, but can also be administered by using general protocols or by mixing with pharmaceutical carriers selected in consideration of the standard pharmaceutical practice. For examples, the pharmaceutical composition of the present invention can be dose via oral, buccal or sublingual administration in the form of tablets containing starch or lactose, capsules alone or with excipients, or elixir or suspension with chemicals for taste masking or coloration. Such liquid formulations can be formulated with pharmaceutically acceptable additives such as suspensions (for instance methyl cellulose, semisynthetic glyceride such as witepsol, mixture of apricot kernel oil and PEG-6 esters, glyceride mixtures such as PEG-8 and caprylic/capric glyceride).

The administration dose of the pharmaceutical composition of the present invention can vary depending on the age, weight, health status and seriousness of the disease of the patient and administration type, and can be once or number of times a day at fixed time interval.

For instance, daily dose of the effective ingredient can be 1~20 mg/kg, and preferably 5~10 mg/kg. The above dose is only an average value, and the dose can be higher or lower depending on the personal differences. It is preferable to have the above dose range since meaningful effect cannot be obtained when the daily dose of the pharmaceutical composition of the present invention is lower than the above dose and it is not only uneconomical, but also can cause undesirable side-effects if the dose is higher.

The method of diagnosing lung adenocarcinoma of the present invention includes the steps of (a) incubating cells in a biological sample with the antibody or its fragment, and (b) detecting the positive immune reaction to the antibody or its fragment.

The biological sample to be detected in the present invention derived from, includes but not limits to, human being and other primates, such as baboon, ape, monkey, etc.; economic animals, such as, bovine, caprine, swine, rabbit, murine, as well as pets, such as feline, canine, etc. The biological sample can be from various bodily fluids and solids, including tissue, cells, blood, saliva, semen, serum, plasma, urine, amniotic fluid, pleural fluid, cerebrospinal fluid, and mixtures thereof. These samples are obtained according to methods well known in the art. Depending on a detection method used, it may be required to manipulate the biological sample to attain optimal reaction conditions. For example, the ionic strength or hydrogen ion concentration or the concentration of the biological sample can be adjusted for optimal immune complex formation, enzymatic catalysis, and the like.

The detection of the positive immune reaction could be confirmed using device detecting the enzyme reaction, fluorescence, luminescence, or radiation. In order to detect the positive immune, the antibody or its fragment may further comprise labeling material which is selected from the group of radioisotopes, toxins, fluorescent materials and staining materials. The examples of the fluorescent materials are fluorescein-5-isothiocyanate (FITC), phycoerythrin(PE), PE-Cy5, and allophycocyanin(APC), but does not limited thereto.

The method of treating lung adenocarcinoma of the present invention includes the step of administering a therapeutically effective amount of the antibody or its fragment to a patient in need of treating lung adenocarcinoma. The method of treating lung adenocarcinoma could optionally include the step of identifying the patient with lung adenocarcinoma before the administration.

In below, the present invention is explained by examples.

The following examples explain the present invention, but the present invention must not be restricted by these examples.

Example 1

Preparation of Recombinant Antigen (CD66c-HuIgFc) by Linking CD66c and $C_H2$-$C_H3$ Human Immunoglobulin Fc Region <1-1> Gene Cloning In order to obtain CD66c-HuIgFc recombinant antigen, a primer for CD66c gene was prepared by defining 34~340 aa region (SEQ ID No: 2) designed by deleting hydrophobic region in CD66c whole cDNA (SEQ ID No: 1), and a primer for Human immunoglobulin Fc region $C_H2$-$C_H3$ (HuIgFc), specifically the base sequence represented by SEQ ID No: 11, was prepared (Table 1).

Figure 2:
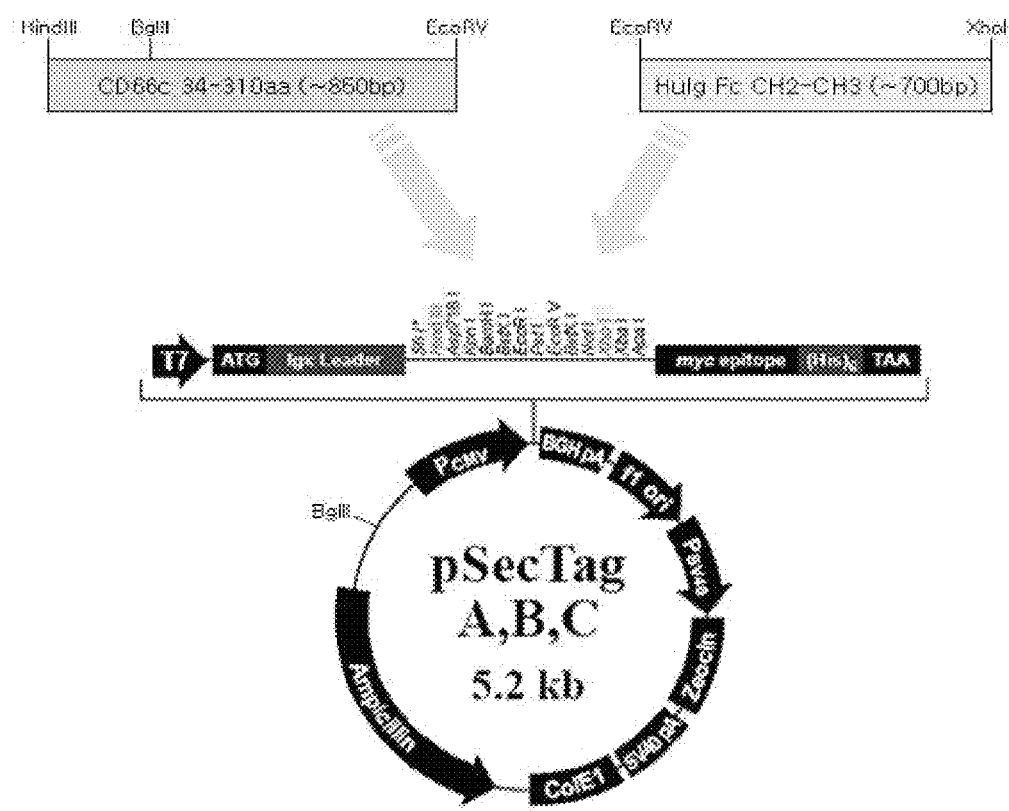
FIG. 2 is a schematic of designing pSegTag-CD66c-HuIgFc cloning.

Schematic for whole cloning procedure is shown in FIG. 2.

TABLE 1

| Gene | Primer | SEG ID | Sequence |
|---|---|---|---|
| CD66c | Hnd66c 5' | SEG ID No: 3 | AAG CTT AAG CTC ACT ATT GAA TCC ACG |
|  | 66cEcRV 3' | SEG ID No: 4 | GAT ATC AGT GAC TGT GGT CCT ATT GA |
| Human Ig Fc (CH2-CH3) | EcrVFc 5' | SEG ID No: 5 | GAT ATC GAC GTC GAG TCC AAA TCT TGT |
|  | FcXhoI 3' | SEG ID No: 6 | CTC GAG TTT ACC CGG AGA CAG GGA GA |

The above CD66c gene was obtained by extracting RNA from human lung adenocarcinoma cell line, A549 (ATCC CCL-185) by using QIAGEN RNEasy Mini spin kit and performing RT-PCR by using primer shown in the above Table 1. Specifically, the above RT-PCR was performed with Novagen first cDNA synthesis kit, and more specifically by reacting RNA 1 ug and Oligo d(T) primer 1 µl (10 pmol/µl) at 70° C. for 10 min, cooling and reacting for 1 hour at 37° C. after adding 5× buffer, 100 mM DTT, reverse transcriptase to synthesize cDNA. The synthesized DNA was amplified by PCR using the primer in Table 1 with PCR premix (Bioneer, Korea) by performing 30 PCR cycles of 1 min at 94° C. and 2 min at 72° C. to obtain CD66c gene.

The result of the above experiment confirmed the 850 bp DNA of CD66c gene that can code the region of DNA in CD66c whole cDNA without the hydrophobic region (FIG. 3a), and the above DNA was cloned in pGEM T (Promega, USA) vector and confirmed by restriction enzyme, EcoRI, and sequenced to confirm the nucleic acid sequence of SEQ ID: 8.

Also the above Human Ig Fc region (HuIgFc) was obtained by extracting RNA using QIAGEN RNEasy Mini spin kit from human B cell (ATCC CTL-1834) and by performing the above RT-PCR using the primer in the above Table 1.

The above CD66c gene cloned pGEM T-CD66c gene was cleaved with HindIII and EcoRV restriction enzyme (Promega, USA) to prepare the insert, and HuIgFc was cleaved with EcoRV and XhoI to prepare two inserts. The pSegTagB (Invitrogen, USA) vector having Igk leader sequence as an expression vector was cleaved with restriction enzymes, HindIII and XhoI and two inserts were inserted simultaneously to complete the cloning.

Figure 3:
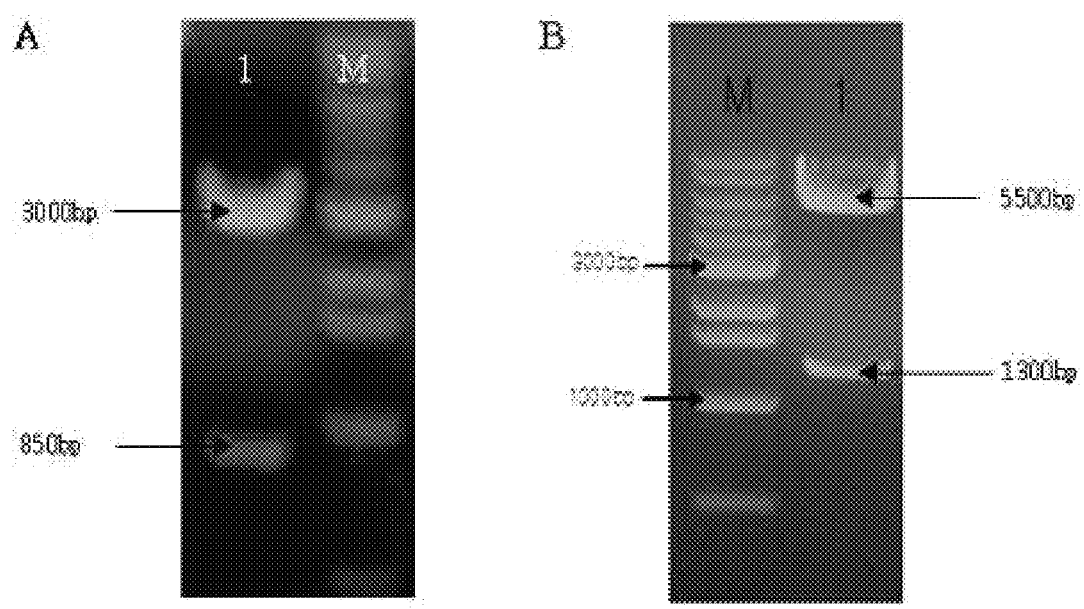
FIG. 3A is a result of confirming the 850 bp DNA of CD66c gene that can code the region of DNA in CD66c whole cDNA without the hydrophobic region.
FIG. 3B is a result of confirming Cloning of CD66c-HuIgFc recombinant DNA by verifying the DNA fragment of 1300 bp by treating the final pSegTagB-CD66c-HuIgFc recombinant DNA with restriction enzyme BgIII.

Cloning of CD66c-HuIgFc recombinant DNA was confirmed by verifying the DNA fragment of 1300 bp treating the final pSegTagB-CD66c-HuIgFc recombinant DNA with restriction enzyme BglII (FIG. 3b).

<1-2> Transfection and Establishment of Stable Cell Line

A cell line expressing recombinant antigen was developed by transfection of CHO-K1 cells (ATCC cells CRL-9618) with pSecTag-CD66c-HuIgFc DNA prepared in the above Example 1-1. Detailed experimental method is as follows.

Firstly, one day before the transfection, CHO-K1 cells were inoculated into 6-well plate at a concentration of $1 \times 10^6$ cells/ml and 3 ml of DMEM medium (Dulbecco's modified Eagle's medium, Gibco, USA) containing 10% Fetal bovine serum (Gibco, USA) was added and cultured for 18 hours at 37° C., under a 5% $CO_2$ condition. pSecTag-CD66c-HuIgFc DNA prepared in the above Example 1-1 was transfected to CHO-K1 cells using Effectene transfection reagent kit (QIAGEN, Hilden, Germany).

Three days after the above transfection, ELISA assay was performed for the supernatant using CD66c and HuIg to evaluate the amount of expressed CD66c-HuIgFc. To prepare stable cell line, selection process was performed using 150 ug/ml of Zeocin (Gibco, USA). After the selection process, single colony was obtained by performing limiting dilution) to establish the final cell line.

<1-3> Purification of Recombinant Antigen

In case of CD66c-HuIgFC recombinant antigen, it is easily expressed by applying Protein G-affinity chromatography to the supernatant of the cell line in the above Example 1-2 which expresses the antigen. Detailed experimental method is as follows.

Supernatant was collected after cultivating the stable cell line selected from the above Example 1-2, and was added with protein G-agarose (Thermo Fisher Scientific Inc. USA) and incubated at 4° C. overnight, and packed into a column and washed with 15 ml of washing buffer (20 mM Phosphate buffer, pH7.2). Afterwards, 5 ml of Elution Buffer (0.1M Glycine, pH 2.9) was added into the column to collect 1 ml fractions, which was neutralized by 100 µl of neutralizing buffer (1M TrisCl, pH 8.0) to obtain the purified CD66c-HuIgFc recombinant protein.

The recombinant protein obtained above was eluted after measuring the absorbance at 280 nm, and dialyzed with Phosphate buffered saline (PBS) solution. The concentration of the protein was determined by Protein Assay Kit (Thermo Fisher Scientific Inc. USA).

Figure 5:
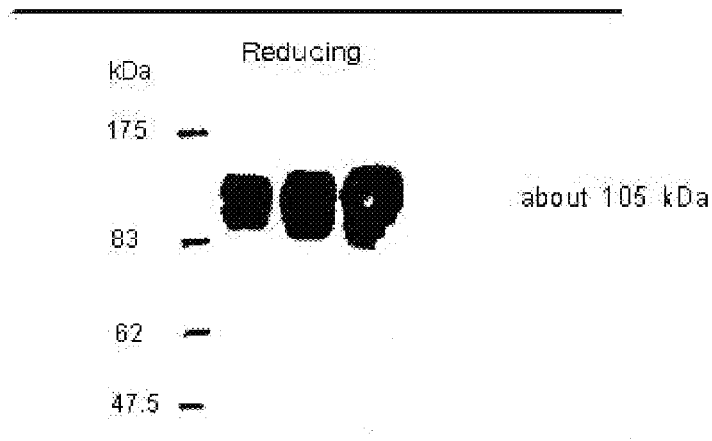
FIG. 5 is a western blot result confirming purified CD66c-HuIgFc recombinant antigens.

After loading 2, 5 and 10 µg of the purified antigen from the above protein G-affinity chromatography into a 10% Trisglycine gel and transferred to nitrocellulose membrane, western blot was performed with human Ig-HRP to confirm the protein with molecular weight of 105 kDa (FIG. 5).

<1-4> Verification of Expression of Recombinant Antigen in Transformation Cell Line In order to verify the expression of CD66c-HuIgFc recombinant antigen in transfected CHO-K1 cell line in the above Example 1-2, three sandwich ELISA was performed by using AP11, an antibody of CD66c, and Goat anti-human Fc fragment and Goat anti-human Ig, antibodies of HuIgFc (refer to Table 2, mAb: monoclonal antibody)

TABLE 2

|  | method #1 | method #2 | method #3 |
|---|---|---|---|
| coating | anti-CD66c mAb (AP11) | anti-Human Ig Fc | anti-Human Ig |
| detecting | anti-Human Ig Fc-HRP | Mouse anti-CD66c mAb | |
| | | Goat anti-mouse IgM-HRP | |

Specifically 96-well micro titration plates (Maxisorp; Nunc, Roskilde, Denmark) were coated with 100 ng/well of AP11 mAb (DiNona, Korea) and 400 ng/well of Goat antihuman Fc fragment, Goat anti-human Ig antibody, each diluted in PBS and incubated for 1 hour at 37° C. Afterwards, the reaction was blocked by adding 200 µl/well of 1× blocking buffer (blocking buffer, Sigma) and incubated for 1 hour at 37° C. One hundred microliters of the supernatant of transfected CHO-K1 cell line in the above Example 1-2 was added to each well to induce binding with the coated antibodies for 1 hour at 37° C., and the unconjugated antibody was removed by washing three times with PBS.

Figure 4:
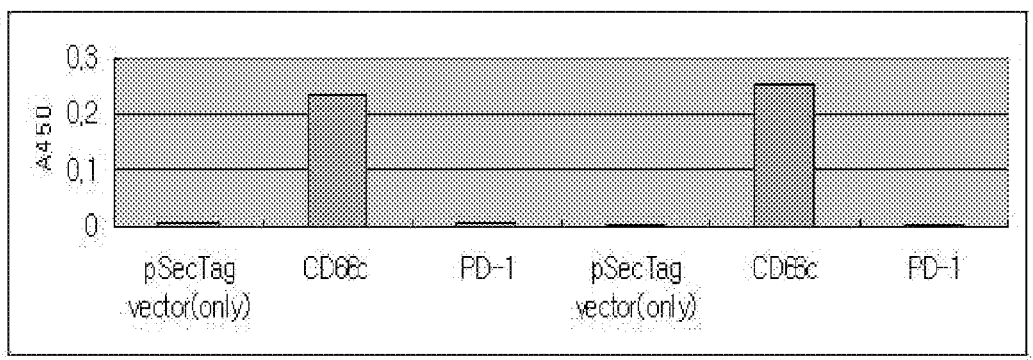
FIG. 4 is a result of confirming the expression of CD66c-HuIgFc recombinant antigen in transgenic CHO-K1 cell line by performing ELISA.
Figure 4:
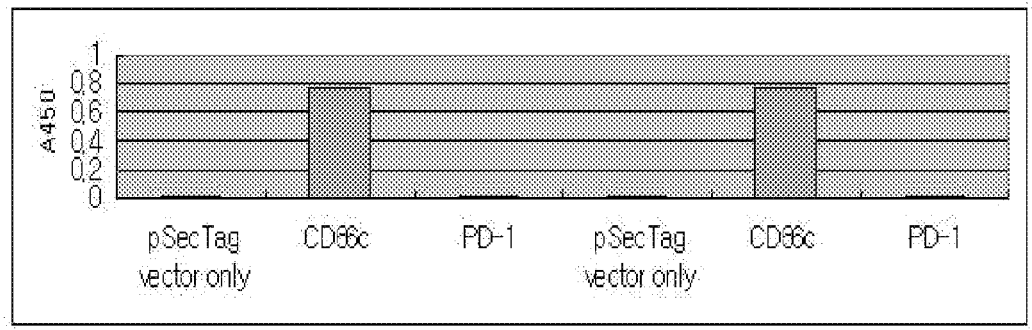
Figure 4:
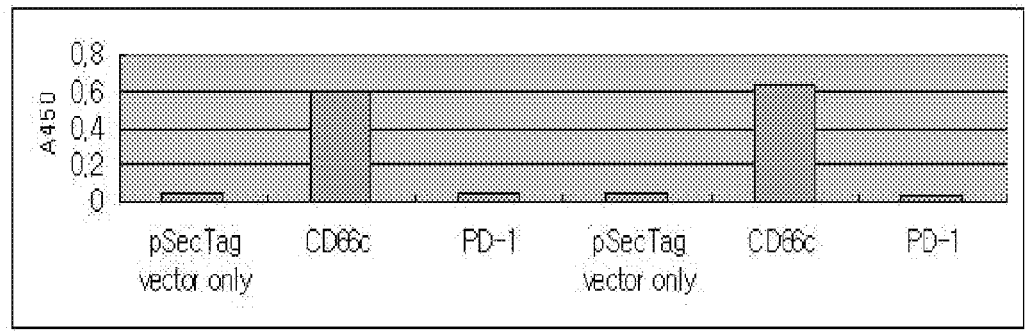

In the above well with conjugated AP11 mAb and supernatant, hydroperoxidase (HRP) conjugated goat anti-human Fc fragment specific Ab (Jackson Immuno Research Laboratories, West Grove, Pa.) was added and reacted for 30 min at 37° C., and in the well with conjugated anti-human Ig Fc, anti-human Ig and supernatant, mouse anti-CD66c mAb was added and reacted for 1 hour at 37° C. The cells were washed 3 times with PBS and added with HRP conjugated goat anti mouse IgM (Jackson Immuno Research Laboratories, West Grove, Pa.) and reacted for 30 min at 37° C. After binding HRP as above, the wells were washed with PBS to remove unconjugated HRP conjugate. After adding 50 µl/well substrate solution and reacted for 10 min at room temperature, the reaction was terminated with 2 N sulfuric acid. The progress of the reaction was monitored by measuring absorbance at 450 nm using ELISA reader, and the result is shown in FIG. 4. As a control group, cell supernatant obtained by transfection of pSegTag vector only and a different antigen, PD1 (DiNona, Korea) conjugated with HuIgFc were used.

As shown in FIG. 4, CD66c-HuIgFc recombinant antigen is expressed in the transformed CHO-K1 cell line in the above Example 1-2.

<1-5> Verification of Function of Recombinant Antigen

Figure 6:
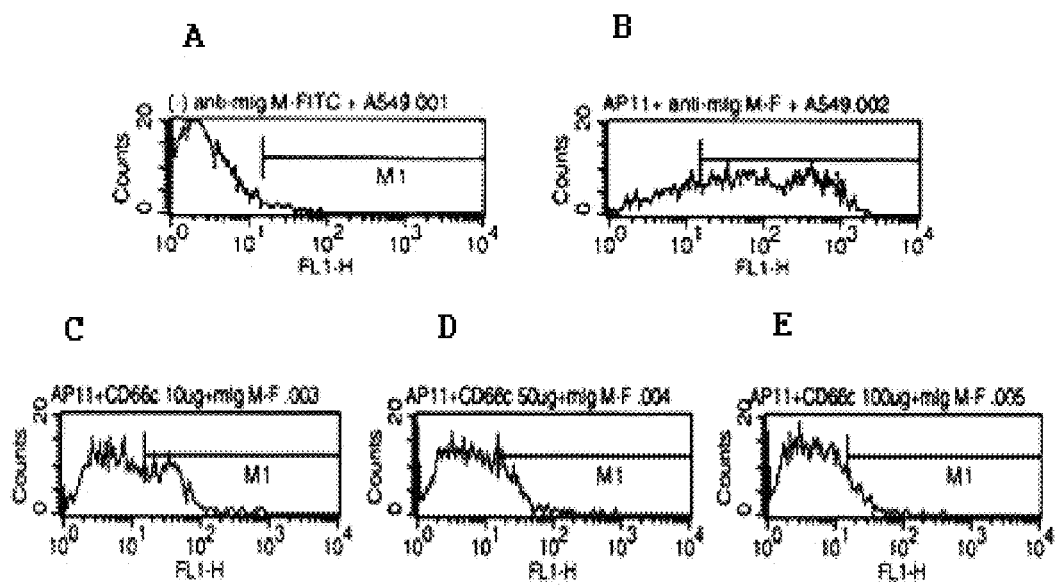
FIG. 6 is a result of confirming CD66c activity of recombinant CD66c-HuIgFc.

In order to confirm whether the purified recombinant antigen (CD66c-HuIgFc) in the above Example 1-3 acts as CD66c antigen, inhibition of conjugation of anti-CD66c antibody, AP11, on the surface of A549 cells by the above recombinant antigen was confirmed by flow cytometry, and the result is shown in FIG. 6.

Specifically, after conjugating 0, 10, 50 and 100 µg of the above recombinant antigen with AP11 antibody for 30 min at 4° C., it was added to A549 cells and reacted for 30 min at 4° C., added with 3 ml of PBS, centrifuged for 3 min at 1500 rpm and washed. To confirm the conjugated antibody, secondary antibody, goat anti-Mouse IgM FITC (DiNona) was diluted 200 times, added, reacted for 15 min at 4° C., washed as above with 3 ml of PBS and measured by flow cytometry.

As shown in the above FIG. 6, positive result is observed for those without CD66c-HuIgFc (FIG. 6b), but blocking was observed proportional to the treated amount when the above recombinant antigen (CD66c-HuIgFc) was conjugated with 10, 50 and 100 µg of anti-CD66c mAb and conjugated subsequently with A549 cells (FIGS. 6c, d and e).

Example 2

Development of Lung Adenocarcinoma Specific Monoclonal Antibody

<2-1> Preparation of Hybridoma Cell and Monoclonal Antibody

Figure 7:
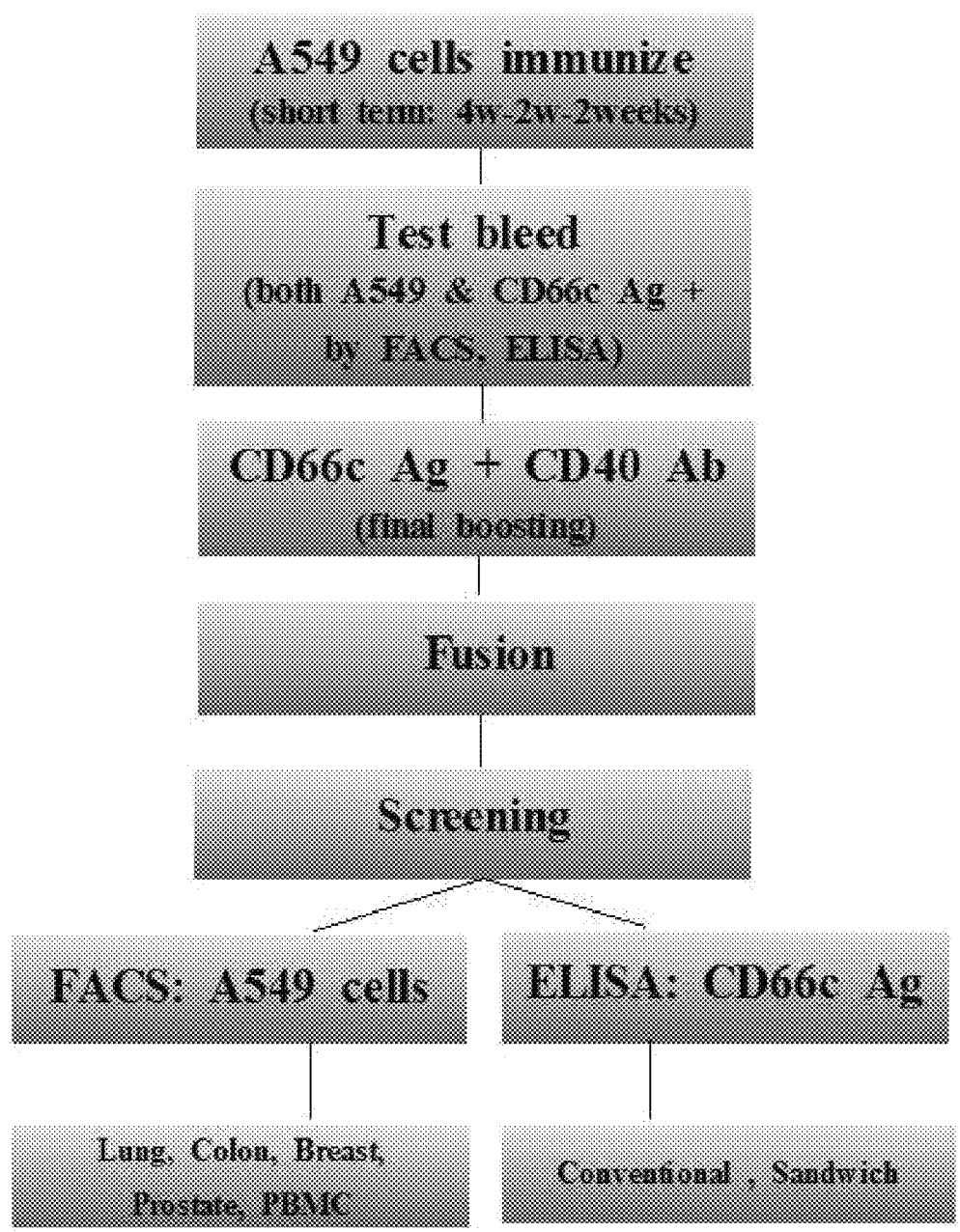
FIG. 7 is a schematic of developing monoclonal antibody for lung adenocarcinoma specific CD66c.

In order to develop monoclonal antibody specific to CD66c expressed in adenocarcinoma, adenocarcinoma A549 cell line was immunized instead of direct immunization of the above recombinant CD66c-HuIgFc, and the above recombinant CD66c-HuIgFc was injected at the boosting stage to amplify antibodies for CD66c. In the selection process of hybridoma, antibody which is positive for both CD66c-HuIgFc and A549 cell was selected to obtain antibody for CD66c expressed in adenocarcinoma (refer to FIG. 7).

Figure 8:
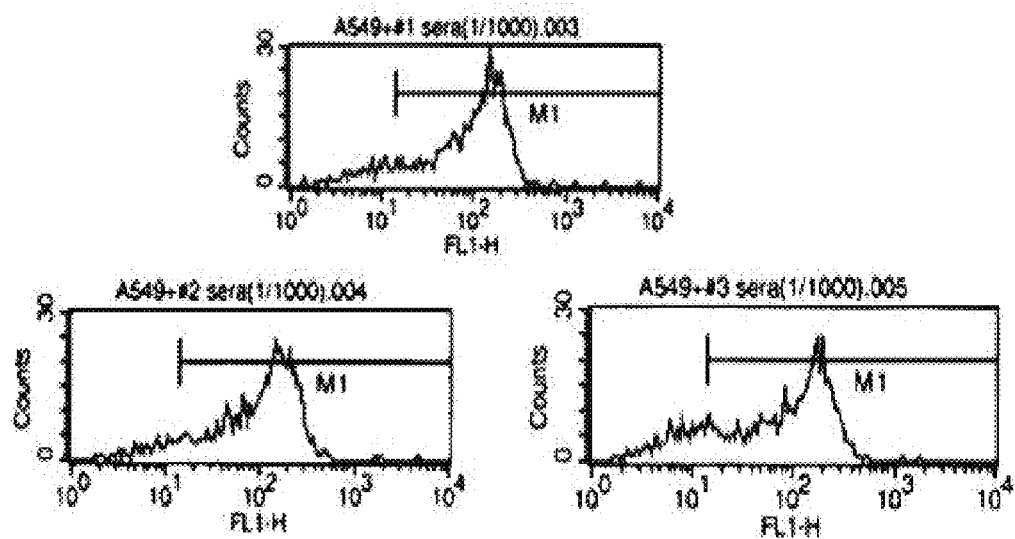
FIG. 8 is a result of confirming titers for A549 cells in the serum of A549 immunized mice.
Figure 9:
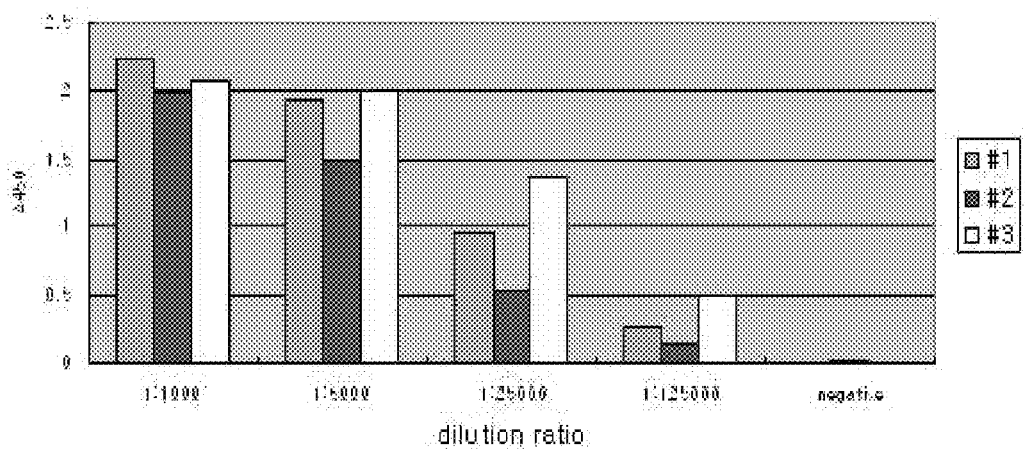
FIG. 9 is a result of confirming titers for CD66c-HuIgFcd in the serum of A549 immunized mice.

In order to develop adenocarcinoma specific monoclonal antibody, $1 \times 10^7$/mouse A549 cells (ATCC CCL-185), adenocarcinoma cell line, was injected into the intraperitoneal cavity of a 6-week old female Balb/c mouse three times in 3-week intervals. Blood samples were obtained from the tail vein to collect the serum. In the above separated serum, purified CD66c-HuIgFc in the above Example 1 was added, reacted for 1 hour at 37° C. for coating and terminated by of adding 200 µl/well of the blocking buffer (sigma). In the coated plate, separated serum was added after dilution, reacted for 1 hour at 37° C., and washed with PBS to remove unconjugated antibody. In order to identify conjugated antibody, secondary antibody, goat anti-Mouse Ig-HRP (Jackson) was diluted by 200 times and added at 100 µl/well, reacted at 37° C., and washed with PBS. After adding 50 μl/well of TMB (3,3',5,5'-tetramethylbenzidene) substrate solution and reacted for 10 min at room temperature, the reaction was terminated with 2 N sulfuric acid (Sigma). The titer was confirmed by measuring absorbance at 450 nm using ELISA reader. Diluted serum was added to A549 cells, reacted for 30 min at 4° C., washed with 3 ml of PBS, centrifuged for 3 min at 1500 rpm, and washed to remove unconjugated antibody. In order to identify conjugated antibody, secondary antibody, goat anti-Mouse Ig-FITC (DiNona) was diluted by 200 times and added, reacted for 15 min at 4° C., washed with 3 ml of PBS and measured with flow cytometry to confirm the titer for CD66c. The results are shown in FIGS. 8 and 9. Specifically, 3 day before the cell fusion, immune response was amplified by adding 50 μg of anti-CD40 agonist mAb and injected with 100 ug of CD66c-HuIgFc to induce the amplification of antibody for CD66c.

As shown in the above FIGS. 8 and 9, the titers for A549 cells are high for all as verified by flow cytometry (FIG. 8), and positive response for CD66c-HuIgFc was high in the A549 cell-immunized serum even though the CD66c antigen is not directly immunized (FIG. 9).

After obtaining single cell suspension from the incised spleen from the above immunized mice, the cells were washed twice with RPMI (GIBCO), and mixed with 0.4% tryphan blue (sigma). The number of cells was counted by tryphan blue assay that counts unstained cells by microscope. SP2/0 (ATCC CRL-1581) or X63 moue myeloma cell line (ATCC CRL-1580) was used as partner cells for cell fusion, and was counted like the above spleen cells, washed and counted.

The above myeloma cells and spleen cells were mixed in 1:5 ratios, and centrifuged to remove the supernatant. One milliliter of 50% of polyethylene glycol 1500 preheated to 37° C. was added slowly. After 1 min delay, RPMI medium was added slowly and diluted sequentially. After centrifugation, cells were suspended in RPMI (20% FBS, hypoxanthine-aminopterin-thymidine) supplemented with 1×HAT, and 100 μl/well of aliquots were added into 96-well plate and cultured in 5% $CO_2$ incubator at 37° C. After the above fusion, HAT feeding was progressed for a certain period of time, and when wells with colony formation was observed, 100 μl of the supernatant is added to A549 cell, adenocarcinoma cell line, reacted for 30 min at 4° C., added with 3 ml of PBS, and centrifuged for 3 min at 1500 rpm to remove unconjugated antibody. In order to confirm conjugated antibody, secondary antibody, goat anti-Mouse Ig-FITC (DiNona) was added after a 200-fold dilution, reacted for 15 min at 4° C., washed with 3 ml of PBS as above and measured by flow cytometry. Purified CD66c-HuIgFc using CD66c-HuIgFc was added at 100 ng/well, coated by reacting for 1 hour at 37° C., and terminated by adding blocking buffer (sigma) at 200 μl/well and reacting for 1 hour at 37° C. In the coated plate, 100 μl/well of hybridoma supernatant was added and reacted for 1 hour at 37° C., and the unconjugated antibody was washed with PBS. Finally, to confirm the conjugated antibody, secondary antibody, goat anti-Mouse Ig-HRP (Jackson) was diluted by 200 times and added at 100 μl/well, and reacted at 37° C. and washed with PBS. After adding 50 μl/well of TMB (3,3',5,5'-tetramethylbenzidene) and reacting for 10 min at room temperature, the reaction was terminated with 2 N sulfuric acid (Sigma). The result was monitored by measuring absorbance at 450 nm to perform enzyme-linked immunosorbent assay (ELISA).

The 8F5 monoclonal antibody showing positive in both of the above two methods was selected, and finally, the hybridoma cells expressing single colony 8F5 mAb was obtained through limiting dilution.

<2-2> Isotype Determination of Monoclonal Antibody

In order to determine the isotype of 8F5 monoclonal antibody prepared in the above Example 2-1, analysis was performed with mouse immunoglobulin isotyping ELISA kit (BD Biosciences, USA). Specifically, isotyping was performed with rabbit anti-murine isotype specific antisera (IgG1, IgG2a, IgG2b, IgG3, IgM, IgA, Kappa, Lambda) and peroxidase-labeled goat anti-rabbit IgG were used as secondary antibody. Color reaction was induced by using orthophenylenediamine(OPD) and hydrogen peroxide substrate and confirmed by measuring the absorbance at 450 nm.

The results confirmed that 8F5 monoclonal antibody is mouse IgG1/kappa light chain (data not shown).

<2-3> Detection of CD66c Antigen Using Monoclonal Antibody

Western blotting was performed for A549 cell lysate and recombinant antigen (CD66c-HuIgFc) by using 8F5 monoclonal antibody of the present invention and anti-CD66c AP11 antibody.

Specifically, after suspending $1\times10^7$ cells of adenocarcinoma cell line, A549 in 100 μl of lysis buffer(1% Nonidet P-40; NP-40 in 50 mM Tris-HCl, pH 7.4, 50 mM EDTA, and 1 mM phenyl-methyl-sulfonyl-fluoride; PMSF), cells were lysed for 15 min at room temperature and centrifuged to remove cell debris, and supernatant was collected to prepare the lysate. After boiling the prepared A549 lysate and recombinant antigen (CD66c-HuIgFc) obtained in the above Example 1 for 3 min, they were loaded to 8% sodium dodecyl sulfate-polyacrylamide gel electrophoresis (SDS-PAGE) under reducing and non-reducing conditions. After electrophoretic transfer onto a nitrocellulose membrane, reaction was blocked with 5% skim milk (sigma) and conjugated to 8F5 or AP11 monoclonal antibody. Those conjugated with 8F5 monoclonal antibody was washed 3 times with PBS and conjugated to peroxidase-conjugated goat anti-mouse IgG (Sigma, Saint Louis, USA). And those treated with AP11 monoclonal antibody was reacted with peroxidase-conjugated goat anti-mouse IgM (Sigma, Saint Louis, USA). After washing the above nitrocellulose membrane with PBS, bands were confirmed with enhanced chemiluminescence detection system (ECL, Amersham, Sweden), and the result is shown in FIG. 10.

Figure 10:
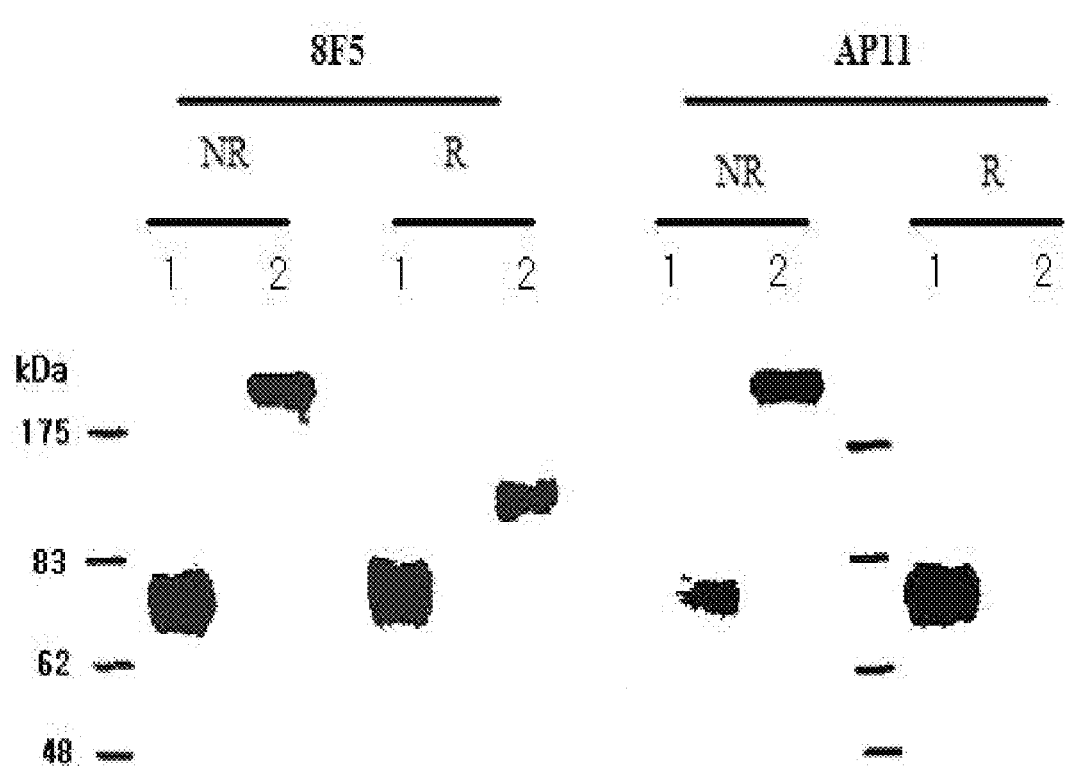
FIG. 10 is a result comparing the western blotting results between 8F5 and AP11.

As shown in FIG. 10, two antibodies were confirmed to show approximately 75 kDa band under non-reduced and reduced conditions. In case of recombinant CD66c-HuIgFc, band was confirmed at 210 kDa for both antibodies under non-reduced condition, and at 105 kDa under reduced condition. The reason for the difference in size for recombinant CD66c-HuIgFc was due to dimer formation in HuIgFc region, but not due to the difference in protein size.

In conclusion, the results of western blotting for the conventional anti-CD66c, AP11 and 8F5 coincide well. Therefore, it is shown that CD66c antigen can be detected by using monoclonal antibody of the present invention.

Meanwhile, CD66c antigen is known to be expressed in granulocytes in blood. Therefore, to confirm the degree of conjugation between peripheral blood and 8F5, after adding 1 μg of 8F5 antibody into peripheral blood mononuclear cells (Korean Red Cross blood centers) and reacted for 30 min at 4° C. and added with 3 ml of PBS, the product was centrifuged for 3 min and washed to remove unconjugated antibodies. In order to confirm conjugated antibody, secondary antibody, goat anti-Mouse Ig-FITC (DiNona) was added after a 200-fold dilution, reacted for 15 min at 4° C., washed with 3 ml of PBS as above and measured by flow cytometry. The result is shown in FIG. 11.

Figure 11:
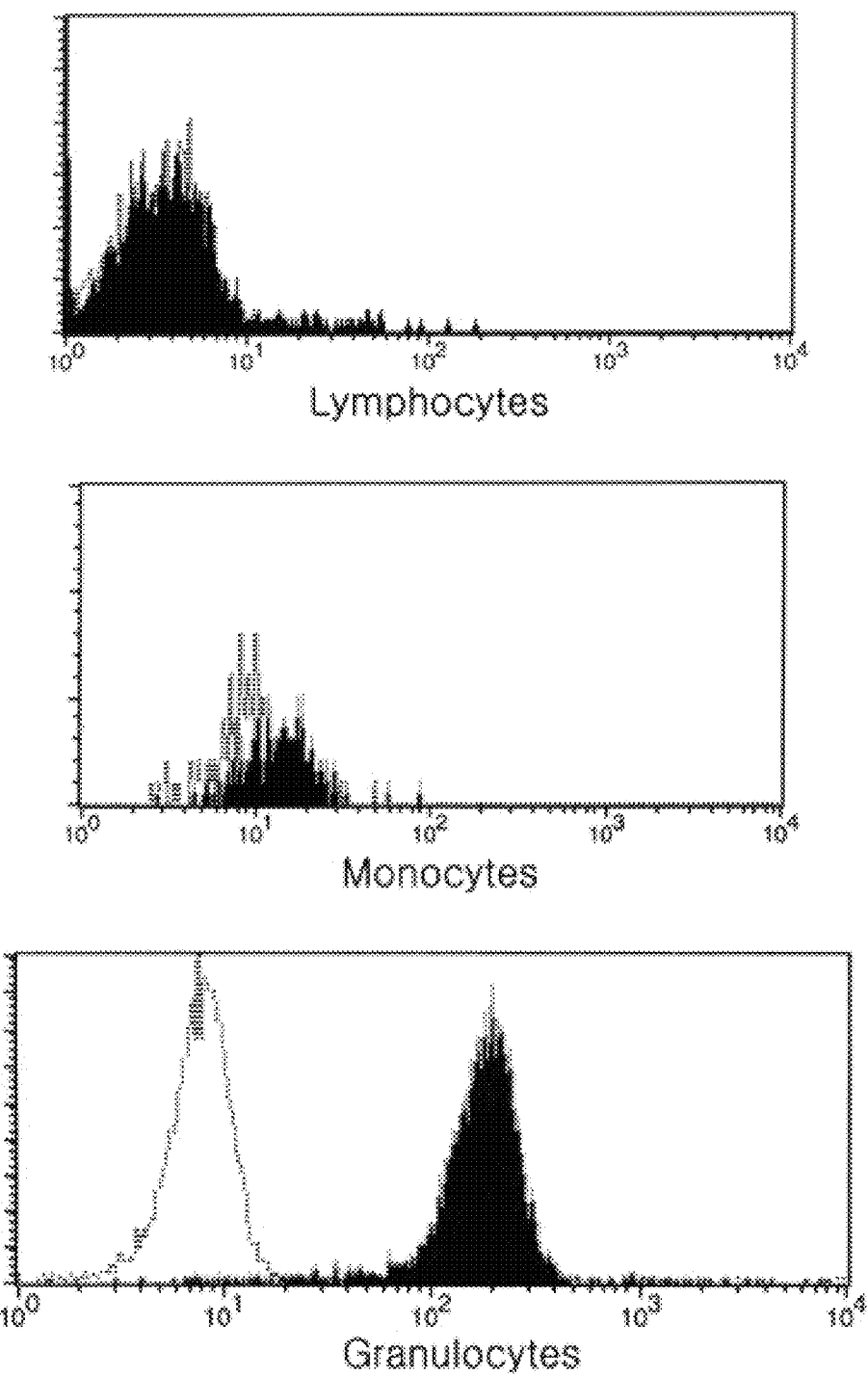
FIG. 11 is a result of the analysis to confirm the binding of 8F5 monoclonal antibody in peripheral blood mononuclear cells.

As shown in the above FIG. 11, CD66c antigen is shown to be expressed by using 8F5 monoclonal antibody in almost all granulocytes at 98% rate, but not in lymphocytes and monocytes.

Also, in order to confirm the conjugation between 8F5 and CD66c-HuIgFc using well-known 9A6 (Santa Cruz, USA) besides AP11 as a monoclonal antibody for anti-CD66c, purified CD66c-HuIgFc was added at 100 ng/well and reacted for 1 hour at 37° C. for coating and blocked by reacting with 200 μl/well of blocking buffer (sigma) 1 hour at 37° C.

In the coated plate, 100 μl/well of 9A6, 8F5 and AP11 antibodies were added and reacted for 1 hour at 37° C., and unconjugated antibody was washed with PBS. Finally, in order to confirm the conjugated antibody, 100 μl/well of the secondary antibody, goat anti-Mouse Ig-HRP (Jackson) was added after a 200-fold dilution, reacted at 37° C., washed with PBS. After adding 50 μl/well of TMB (3,3',5,5'-tetramethylbenzidene) substrate solution and reacted for 10 min at room temperature, the reaction was terminated with 2 N sulfuric acid (Sigma). The result was monitored by measuring absorbance at 450 nm using ELISA reader, and is shown in FIG. 12.

Figure 12:
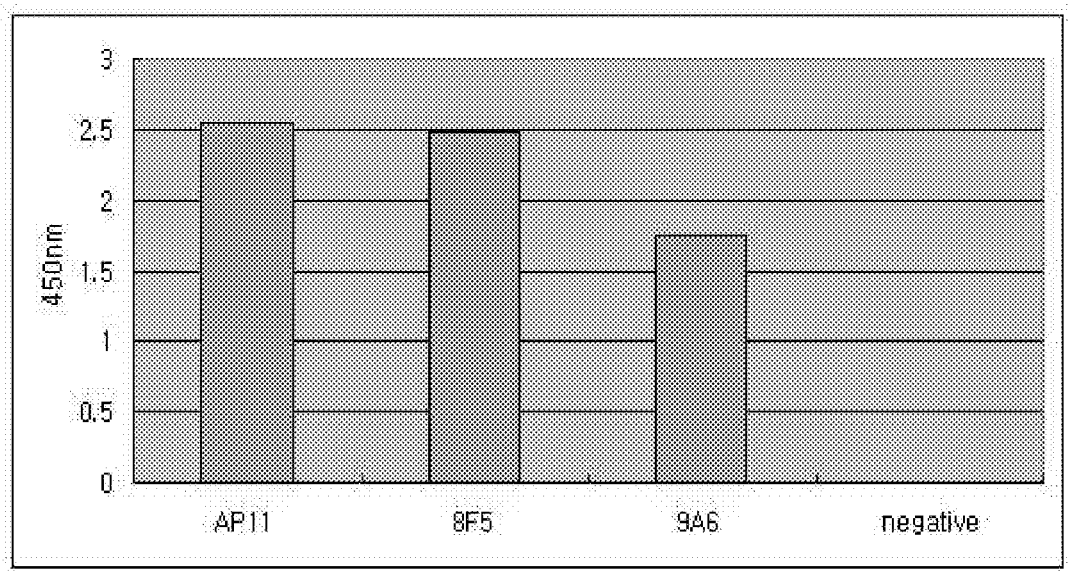
FIG. 12 is a result of ELISA analysis for CD66c-HuIgFc.

As shown in the above FIG. 12, all 3 antibodies have high values for CD66c-HuIgFc, but the activities of three clones are different.

<2-4> Analysis of Expression of CD66c Antigen in Lung Adenocarcinoma Cell Line Using 8F5 Monoclonal Antibody Binding of 8F5 monoclonal antibody to a variety of cancer cell lines obtained from KCLB (Korean Cell Line Bank) and SNU (Seoul National University) was confirmed by flow cytometry.

Specifically, cancer cell lines were obtained from Korean Cell Line Bank and Seoul National University. L-132, SW-900, DU145, LNCap, MDA-MB231 and MCF-7 were cultured in Dubco's MEM (GIBCO, Invitrogen) medium supplemented with 10% heat inactivated fetal bovine serum (FBS; GIBCO, Invitrogen) and A549, NCI-H460, NCI-H417, DLD-1, HCT116, HT-29, SW-480, SW-620 and PC-3 were cultured in RPMI 1640 (GIBCO, Invitrogen) medium supplemented with 10% heat inactivated FBS in an incubator at 37° C. under 5% $CO_2$ conditions.

After culturing the above cultured cancer cell lines by adding 8F5 monoclonal antibody of the present invention for 30 min at 4° C. and washing with PBS, FITC-conjugated goat anti-mouse Ig G (DiNona Inc, Korea) was added for culture for 15 min at 4° C. After washing it again with PBS, the result was analyzed by FACScaliber (Becton Dickinson, USA) and is shown in Table 3.

TABLE 3

| Cell line | Origin | Result |
|---|---|---|
| L-132 | Lung normal | − |
| A549 | Lung adenocarcinoma | +++ |
| NCI-H460 | Squamos lung cancer | − |
| SW-900 | Large cell lung cancer | − |
| NCI-H417 | Small cell lung cancer | − |
| DLD-1 | Colon cancer | − |
| HCT116 | Colon cancer | − |
| HT-29 | Colon cancer | + |
| SW-480 | Colon cancer | − |
| SW-620 | Colon cancer | − |
| MDA-MB-231 | Breast cancer | − |
| MCF7 | Breast cancer | − |
| LN Cap | Prostate cancer | − |
| Du-145 | Prostate cancer | − |
| PC-3 | Prostate cancer | − |

The percentage of 8F5 positive cells among 5000 cells were performed by FACS analysis
−: less than 10% of positive cells
+: 10~25%, ++: 25~50%, +++: 50~75%, ++++: 75~90%

As shown in above Table 3, 8F5 monoclonal antibody of the present invention binds highly in adenocarcinoma cell line A549, but not at all in 4 colon cancer cell lines, 3 prostate cell lines, 2 breast cancer cell lines except for normal lung cell line, L-132 and small cell carcinoma cell line, NCI-H417 and weakly in colon cancer cell line, HT-29.

<2-5> Analysis of Expression of CD66c Antigen in Lung Cancer Tissues Using 8F5 Monoclonal Antibody Immunohistochemical staining for 8F5 was performed with the frozen tissues of normal thymus, lymph node, tonsil, spleen, kidney, urethra and skin obtained from Chungbuk National University Hospital. Clinical lung cancer tissues were fixed with 10% formalin (sigma) and embedded into paraffin.

Figure 13:
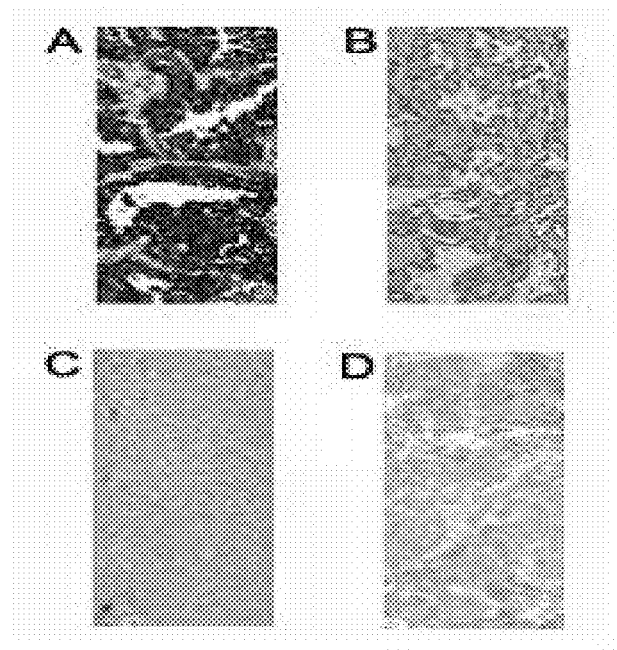
FIG. 13 is a result to confirm the 8F5 staining in lung cancer specimen.

Specifically, tissue staining was performed by adding 8F5 monoclonal antibody into blocking buffer (4% skim milk, 0.1% Tween-20, PBS), reacted overnight at 4° C., added with biotinylated goat anti-mouse IgG and HRP conjugated streptavidin (Dako, Denmark) for conjugation for 20 min at room temperature. Color reaction was performed by using 3,3'-diaminobenzidine (Sigma, Saint Louis. USA), and the results are shown in Table 4 and FIG. 13.

TABLE 4

| | Tymus | Lymph-node | Tonsil | Spleen | Kidney | Urethra | Skin |
|---|---|---|---|---|---|---|---|
| Cortex | − | − | − | − | − | − | − |
| Medulla | − | − | − | − | − | − | − |
| B cell | − | − | − | − | − | − | − |
| T cell | − | − | − | − | − | − | − |
| Epithelium | − | − | − | − | − | − | − |
| Endothelium | − | − | − | − | − | − | − |
| Tubular | − | − | − | − | − | − | − |
| GM | − | − | − | − | − | − | − |
| GC | − | − | − | − | − | − | − |
| SE | − | − | − | − | − | − | − |
| ECC | − | − | − | − | − | − | − |
| KR | − | − | − | − | − | − | − |

Various human frozen tissues were stained by immunohistochemical method. All of them were not expressed.

As shown in the above Table 4, 8F5 monoclonal antibody staining is negative for all of the normal frozen tissues obtained through Chungbuk National University Hospital.

However, brown positive response was confirmed in the lung adenocarcinoma tissues (FIGS. 13a and b), and negative response was observed for squamous cell carcinoma tissue (FIG. 13c) and small cell carcinoma tissues(FIG. 13d) proving that 8F5 monoclonal antibody of the present invention can be used for the detection of lung adenocarcinoma tissue.

Example 3

Epitope Determination of Monoclonal Antibody of the Present Invention

<3-1> Epitope Determination of Monoclonal Antibody of the Present Invention

In order to determine the epitope of 8F5 antibody, monoclonal antibody prepared in the above Example 2 of the present invention, protein peptide analysis using MOLDI-TOF was utilized.

First, after adding 2 to 5 μg of the above 8F5 antibody and 20 μl of Protein A resin (Amersham Pharmacia) for binding for more than 12 hours at 4° C., 500 μl of A549 lysate was added and rotated for more than 4 hours at 4° C., and proteins that were not bound to antibody was removed by washing with PBS to obtain proteins bound to the antibody in protein A resin. Protein was loaded to SDS-PAGE gel to separate proteins, trypsinized and performed with MOLDI-TOF (Mass spectrometric sequencing of proteins silver-stained polyacrylamide gels. Shevchenko A, Wilm M, Vorm O, Mann M. Anal Chem. 1996 Mar. 1; 68(5):850-8.) to analyze the peptides. The computer screen of the above analysis was captured in FIG. 14.

Figure 14:
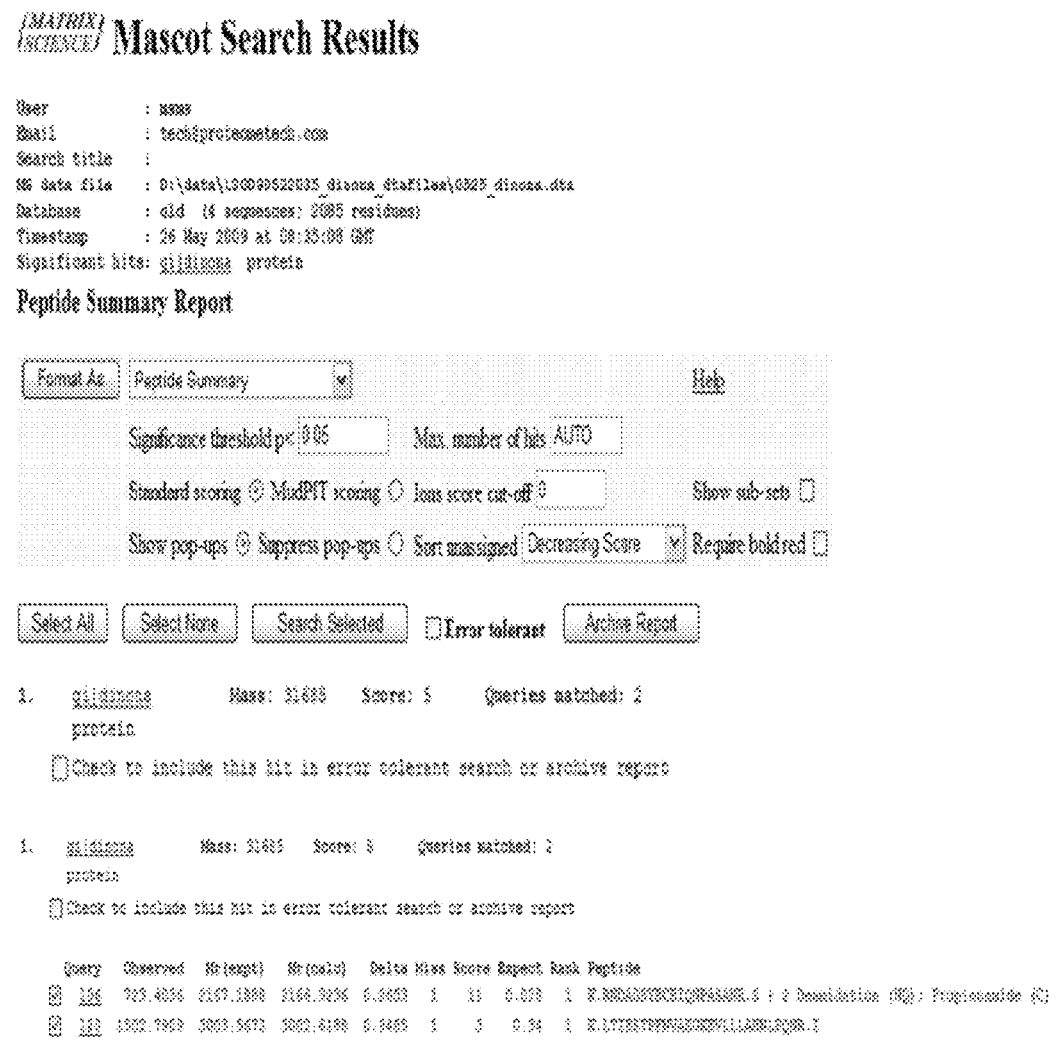

As shown in FIG. 14, the epitope of the monoclonal antibody of the present invention is represented by amino acid sequence of SEQ ID No: 7 (RNDAGSYECEIQNPASANR).

<3-2> Epitope Verification of Monoclonal Antibody of the Present Invention

Figure 15:
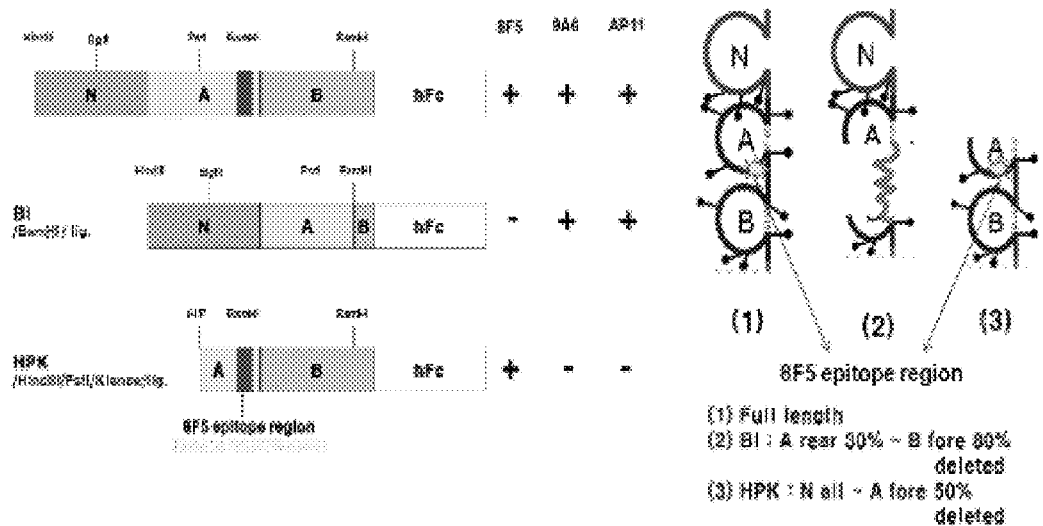
FIG. 15 is a schematic of the verification method of epitope of the monoclonal antibody of the present invention.

It was confirmed that antigen for 8F5 antibody is CD66c by the above proteomic analysis in the above Example 3-1. To verify its epitope, recombinant antigens with or without epitope region determined in the above Example 3-1 were prepared to evaluate the immune response for 8F5 antibody as shown in FIG. 15.

<3-2-1> Preparation of CD66c Mutant Recombinant DNA

CD66c mutant recombinant DNA was prepared using restriction enzyme BamHI existing in the epitope region of 8F5 antibody with pSec-Tag-CD66cfull-hFc recombinant DNA. Specifically, whole base sequence of the above CD66c antigen represented by SEQ ID No: 8 and hFc-conjugated gene were inserted to pSec-Tag, and this was ligated using restriction enzyme BamHI existing in the epitope region of 8F5 antibody to obtain CD66c mutant recombinant DNA.

More specifically, CD66c mutant (BI/BHI) that does not include epitope for 8F5 antibody was ligated with BamHI, and the above 252 bp between 535 and 787 bp of CD66c gene of SEQ ID No: 8 was removed and the rest of the fragment was connected again for the preparation. The sequence of CD66c mutant (BI/BHI) as prepared above is represented as SEQ ID No: 9.

Meanwhile, CD66c mutant (HPK/HdIII/PstI/klenow) which includes epitope of 8F5 antibody, but lacks parts of N domain and A domain in the N-terminus was prepared by ligation with Hind III and PstI, by removing 479 bp fragment from the N-terminus, by treating the rest of the gene fragment with Klenow to fill-in the sticky end for the HindIII and PstI to connect the blunt ends with each other. The sequence of CD66c mutant (HPK/HdIII/PstI/klenow) prepared as above is represented by SEQ ID No: 10.

<3-2-2> Expression of CD66c Mutant Recombinant DNA

The pSec-Tag vector inserted with the above CD66cfull-hFc, CD66c mutant (BI/BHI)-hFc, CD66c mutant (HPK/HdIII/PstI/klenow)-hFc was inserted into CHO-K1 cells using Effectene (Qiagen) for transformation.

More specifically, each of the above genes and Effectene complex were plated overnight, and sprayed with CHO cells with new media and cultivated for 48 hours. Two days after the above transfection, supernatant was obtained to confirm the expression by using sandwich ELISA for the detection of human Fc (hFc) (data not shown).

<3-2-3> Epitope Verification of the Monoclonal Antibody of the Present Invention In order to verify epitope of CD66c for monoclonal antibody of the present invention, conventional anti-CD66c antibodies, 9A6 (Santa cruz) and AP11 (DiNona), were added in each well at 100 ng and reacted for 1 hour at 37° C. to coat as a capture antibody, and blocked by adding 200 µl of 1× blocking solution (sigma) and reacted for 1 hour at 37° C. After adding 100 µl/well of supernatants of CD66c full-hFc, CD66c mutant(BI/BHI)-hFc and CD66c mutant (HPK/HdIII/PstI/klenow)-hFc prepared in the above Example 3-2-2 in the above prepared plate and reacting for 1 hour at 37° C., unconjugated antibody was removed by washing with PBS. In this, diluted anti-human Ig-HRP (Jackson) was added and reacted for 1 hour, wells were washed with PBS. TMB solution was added at 50 µl/well and reacted for 10 min, and the reaction was terminated by adding 50 µl of sulfuric acid to measure absorbance at 450 nm. To confirm the existence of CD66c mutant-hFc protein in the above supernatant, anti-human Ig antibody was used as a control group in Capture & Detect Sandwich ELISA. The results of the above experiment are shown in Table 5 and FIG. 16.

TABLE 5

| | | Capture antibody | | | |
|---|---|---|---|---|---|
| | | 8F5 | 9A6 | AP11 | a-huIg |
| media supernatant | CD66c full-hFc | 2.873 | 2.838 | 2.913 | 3.123 |
| | CD66c mutant(HPK/HdIII/PstI/klenow)-hFc | 2.804 | 0.049 | 0.097 | 3.113 |
| | CD66c mutant(BI/BHI)-hFc | 0.019 | 1.924 | 2.662 | 3.149 |
| | negative | 0.017 | 0.027 | 0.247 | 3.161 |

Figure 16:
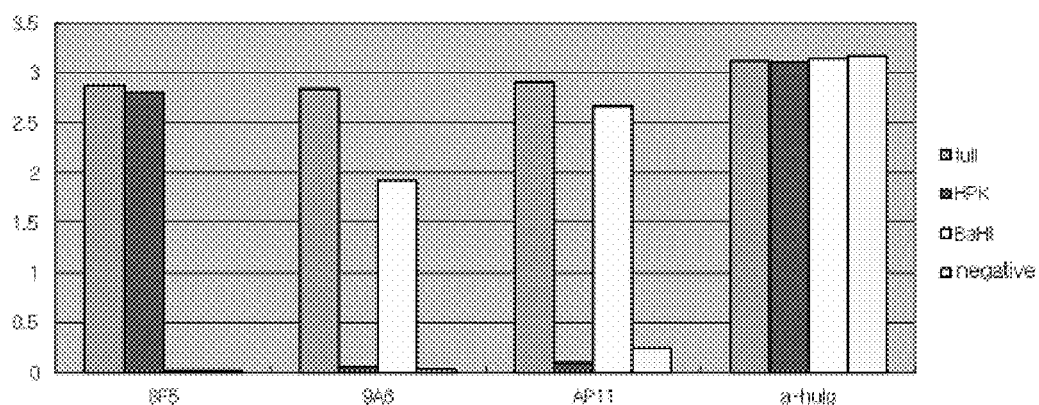
FIG. 16 is a result of verifying the epitope of the monoclonal antibody of the present invention.

As shown in the above Table 5 and FIG. 16, 8F5 antibody of the present invention has an activity to bind to CD66c full-hFc or CD66c mutant(HPK/HdIII/PstI/klenow)-hFc that contains the epitope verified in the above Example 3-1, but binds hardly with CD66c mutant(BI/BHI)-hFc without the above epitope. 9A6 and AP11, conventional CD66c antibodies, however, bonds mainly to CD66c mutant(BI/BHI)-hFc without the above epitope. Therefore, 8F5 antibody of the present invention is represented by a different epitope, amino acid sequence of SEQ ID No: 7, form the conventional 9A6 or AP11 antibody.

Figure 17:
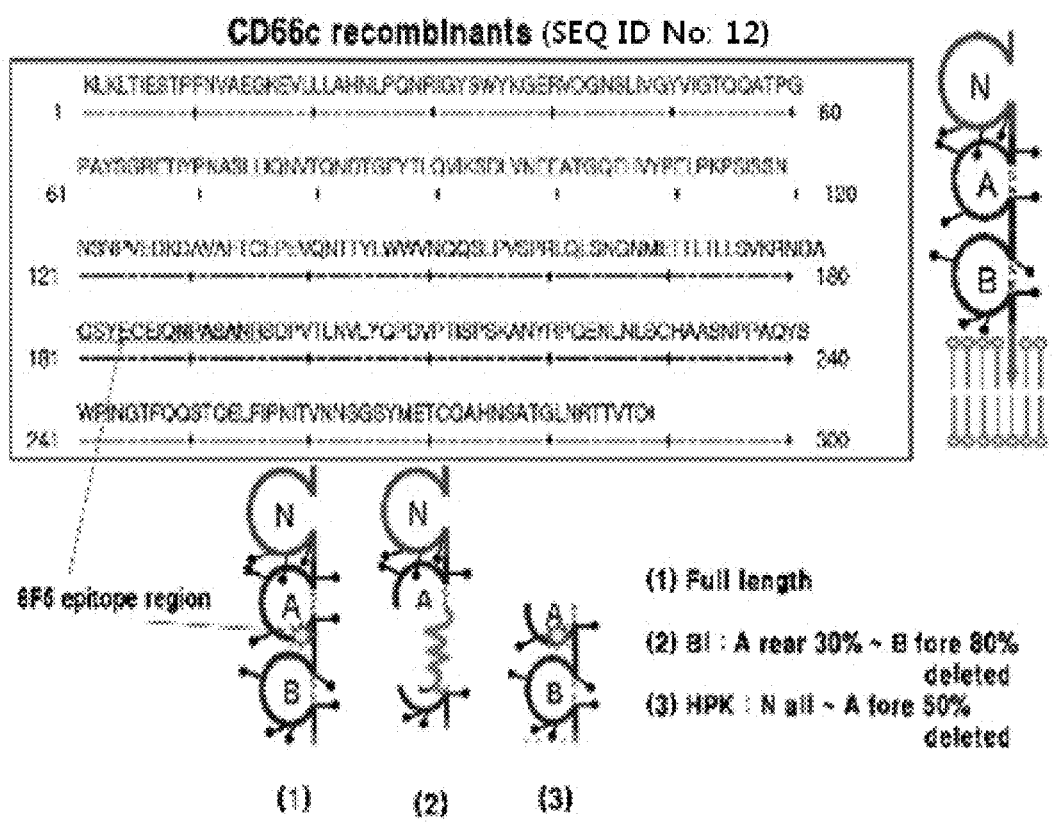
FIG. 17 is a schematic to compare the epitope of the present invention elucidated by MOLDI-TOF and the verification results of the same.

The above experimental result agrees accurately with epitope region of 8F5 antibody identified by MOLDI-TOF as shown in FIG. 17.

Example 4

Detection of Lung Adenocarcinoma Using Monoclonal Antibody of the Present Invention CD66c antigen was detected by using the monoclonal antibody of the present invention by immunoassay.

Specifically, AP11, a conventional antibody of CD66c was added at 100 ng/well and reacted for 1 hour at 37° C. to coat as capture antibody, and blocked by reacting with 200 µl/well of 1× blocking solution (sigma) for 1 hour at 37° C. In this prepared plate, 100 µg each of lysates of A549, an lung adenocarcinoma cell line, H417, a leukemia cell line, KatoIII (ATCC HB-103), a stomach cancer cell line, and K562 (ATCC CCL-243), a leukemia cell line were added and reacted for 1 hour at 37° C., and unconjugated antibody was removed by washing with PBS. In this, antibody prepared by conjugation of 8F5 antibody and HRP was added and reacted for 1 h. The plate was washed with PBS, reacted for 10 min after adding 50 µl/well of TMB solution and the reaction was terminated by adding 50 µl/well of sulfuric acid to read the value at 450 nm. The value (detection Ag) was determined quantitatively by using CD66c full-hFc as a standard, and the result is shown in FIG. 18.

Figure 18:
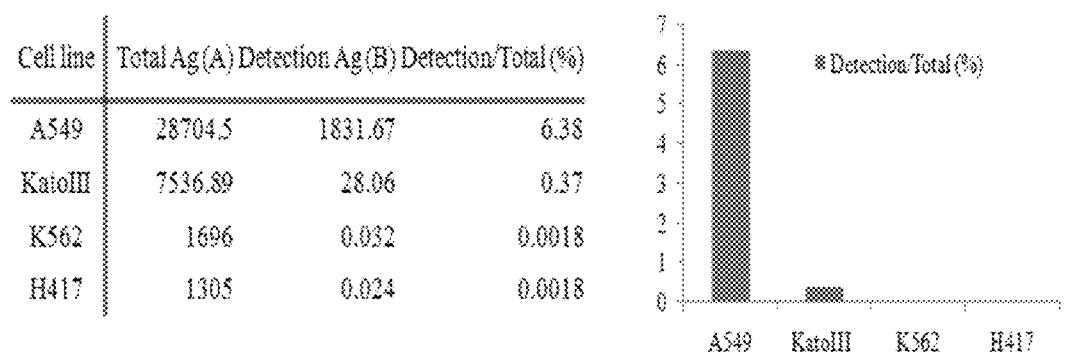
FIG. 18 is a result of detecting lung adenocarcinoma including CD66c antigen by using the monoclonal antibody of the present invention.

As shown in FIG. 18, lung adenocarcinoma can be detected efficiently by using 8F5 antibody of the present invention, and therefore it can be concluded that 8F5 antibody of the present invention is a effective lung adenocarcinoma specific biomarker.

Example 5

Anticancer Activity of Monoclonal Antibody of the Present Invention

Six-week old (18 g) male Nude-mouse (Central Lab. Animal Inc., Korea) was used for the experiment. A549, a lung adenocarcinoma cell line was suspended by using 1× trypsin-EDTA (GIBCO) and washed twice with Hanks balanced salt solution (HBSS) to inject 1×10$^7$ cell per mouse at the backside of the front leg at a volume of 100 μl to obtain inoculated mice. Before metastasis occurs, fast-growing tumor specimens with sufficient blood supply were obtained. The location of tumor was identified by touch on the skin, and the growth was observed at least twice a week, and the mice with 100 mm$^3$ of tumor mass in volume were used for the experiment.

To acquire high level of statistical significance, mice with higher than 100 mm$^3$ of tumor mass in volume were selected, and 10 mice were assigned per group. Monoclonal antibody of the present invention was diluted by 1×PBS and injected at a dose of 100 ug/100 ul, and administered for total 7 times at injection interval of 0, 3, 7, 14, 21, 28 and 35 days.

Figure 19:
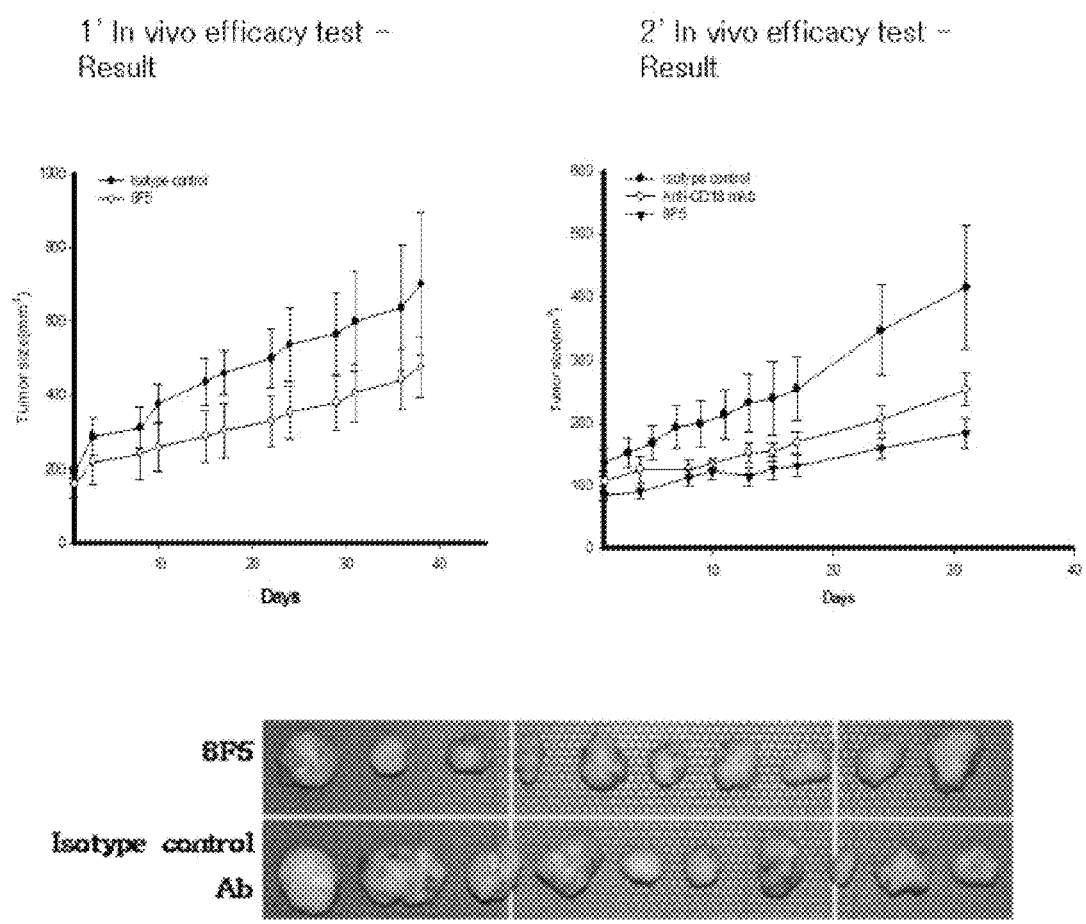
FIG. 19 is a result of anticancer activity of the monoclonal antibody of the present invention.

Volume of the tumor was estimated by measuring long and short axes with calipers twice a week starting at the administration day of the monoclonal antibody of the present invention for 4~5 weeks to verify the effect of the samples, and the result is shown in FIG. 19.

As shown in FIG. 19, 8F5 antibody of the present invention is an antibody that does not have antigen expressed in A549 cells, and has more than 30% higher anticancer effect than isotype control antibody (DiNona) which has same isotype with 8F5.

REFERENCE TO DEPOSITED BIOLOGICAL MATERIAL

Depository Institution: Korean Cell Line Research Foundation
Deposition number: KCLRF BP00230
Date of deposition: Feb. 22, 2010

What is claimed is:

1. An isolated antibody or its antigen binding fragment specifically binding an isolated polypeptide consisting of the amino acid sequence of SEQ ID NO:7 as an epitope of CD66c (Cluster of Differentiation 66c).

2. The isolated antibody or its antigen binding fragment of claim 1 wherein the antibody is a monoclonal antibody.

3. The antibody or its antigen binding fragment of claim 2 wherein the monoclonal antibody is produced by hybridoma cell with a deposition number: KCLRF-BP-00230.

4. A cell line producing the antibody or its antigen binding fragment of claim 1.

5. The cell line of claim 4 wherein the cell line is a hybridoma cell with a deposition number: KCLRF-BP-00230.

6. A composition for diagnosing lung adenocarcinoma comprising the antibody or its antigen binding fragment of claim 1 as an effective ingredient.

7. A diagnostic kit for lung adenocarcinoma comprising the antibody or its antigen binding fragment of claim 1 as an effective ingredient.

8. A pharmaceutical composition for treating lung adenocarcinoma comprising the antibody or its antigen binding fragment of claim 1 as an effective ingredient.

9. A method of diagnosing lung adenocarcinoma comprising incubating cells in a biological sample with the antibody or its fragment of claim 1, and detecting the positive immune reaction to the antibody or its fragment.

10. The method of diagnosing lung adenocarcinoma according to claim 9, wherein the detection of the positive immune reaction is confirmed using device detecting the enzyme reaction, fluorescence, luminescence, or radiation.

11. A method of treating lung adenocarcinoma comprising administering a therapeutically effective amount of the antibody or its fragment of claim 1 to a patient in need of treating lung adenocarcinoma.

* * * * *